United States Patent
Paul et al.

(10) Patent No.: US 7,674,598 B2
(45) Date of Patent: *Mar. 9, 2010

(54) METHOD FOR A FULLY AUTOMATED MONOCLONAL ANTIBODY-BASED EXTENDED DIFFERENTIAL

(75) Inventors: Ronald D. Paul, Fort Lauderdale, FL (US); Oilda Rubio, Miami, FL (US); Diana B. Careaga, Miami, FL (US); Lidice L. Lopez, Miami, FL (US); Ravindra Mylvaganam, Longmeadow, MA (US)

(73) Assignee: Beckman Coulter, Inc., Fullerton, CA (US)

( * ) Notice: Subject to any disclaimer, the term of this patent is extended or adjusted under 35 U.S.C. 154(b) by 478 days.
This patent is subject to a terminal disclaimer.

(21) Appl. No.: 11/475,313

(22) Filed: Jun. 27, 2006

(65) Prior Publication Data
US 2006/0269970 A1 Nov. 30, 2006

Related U.S. Application Data

(63) Continuation-in-part of application No. 11/130,492, filed on May 17, 2005.
(60) Provisional application No. 60/573,167, filed on May 21, 2004.

(51) Int. Cl.
*G01N 33/567* (2006.01)
(52) U.S. Cl. .................. 435/7.24; 435/7.1; 435/7.21; 435/7.23; 435/285.2; 435/287.1; 435/287.2; 435/288.7; 436/10; 436/17; 436/56; 436/164; 436/171; 436/175; 436/546; 422/82.01; 422/82.05; 422/82.07
(58) Field of Classification Search ............... 435/2, 435/7.24, 7.25, 40.5, 239, 285.2, 287.1, 287.2, 435/288.7, 962, 7.21, 7.23; 436/10, 17, 56, 436/63, 164, 165, 171, 174, 175, 176, 177, 436/526, 532, 533, 546, 536; 422/82.01, 422/82.05, 82.06, 82.07, 90, 91
See application file for complete search history.

(56) References Cited

U.S. PATENT DOCUMENTS
3,962,125 A 6/1976 Armstrong
(Continued)

FOREIGN PATENT DOCUMENTS
EP 0317156 5/1989
EP 1363126 11/2003

OTHER PUBLICATIONS

Burgess, "Continuing Absolute Numbers of Specific Leukocyte Subpopulations in Avian Whole Blood Using a Single-Step Flow Cytomeric Technique: Comparison of Two Inbred Lines of Chickens", J of Immunol, 227 (1-2):169-176 (Jul. 30, 1999).
(Continued)

*Primary Examiner*—Gailene R Gabel
(74) *Attorney, Agent, or Firm*—Howson & Howson LLP; Mitchell E. Alter, Esq.

(57) ABSTRACT

Methods for differentially identifying cells in an instrument employ compositions containing a combination of selected antibodies and fluorescent dyes having different cellular distribution patterns and specificities, as well as antibodies and fluorescent dyes characterized by overlapping emission spectra which form non-compensatable spectral patterns. When utilizing the compositions described herein consisting of fluorescent dyes and fluorochrome labeled antibodies with overlapping spectra that cannot be separated or distinguished based upon optical or electronic compensation means, a new fluorescent footprint is established. This new fluorescent footprint is a result of the overlapping spectra and the combined cellular staining patterns of the dyes and fluorochrome labeled antibodies chosen for the composition. The new fluorescent footprint results in histogram patterns that are useful for the identification of additional cell populations or subtypes in hematological disease.

24 Claims, 12 Drawing Sheets

U.S. PATENT DOCUMENTS

| | | | |
|---|---|---|---|
| 5,030,554 | A | 7/1991 | Quintana et al. |
| 5,047,321 | A * | 9/1991 | Loken et al. .................... 435/6 |
| 5,064,616 | A | 11/1991 | Brosnan et al. |
| 5,125,737 | A | 6/1992 | Rodriguez et al. |
| 5,137,809 | A | 8/1992 | Loken et al. |
| 5,164,311 | A | 11/1992 | Gupta |
| 5,234,816 | A | 8/1993 | Terstappen |
| 5,438,003 | A | 8/1995 | Colella et al. |
| 5,563,070 | A | 10/1996 | Yamamoto et al. |
| 5,565,499 | A | 10/1996 | Klemarczyk et al. |
| 5,631,165 | A | 5/1997 | Chupp et al. |
| 5,633,167 | A | 5/1997 | Fan et al. |
| 5,648,225 | A | 7/1997 | Kim et al. |
| 5,763,280 | A | 6/1998 | Li et al. |
| 5,776,709 | A | 7/1998 | Jackson et al. |
| 5,812,419 | A | 9/1998 | Chupp et al. |
| 5,882,933 | A | 3/1999 | Li et al. |
| 6,228,532 | B1 | 5/2001 | Tsuji et al. |
| 6,228,652 | B1 | 5/2001 | Rodriquez et al. |
| 6,461,825 | B1 | 10/2002 | Carriere et al. |
| 6,573,102 | B2 | 6/2003 | Li et al. |
| 6,692,968 | B2 | 2/2004 | Burshteyn et al. |
| 6,900,023 | B1 * | 5/2005 | Houwen et al. ............ 435/7.24 |
| 6,911,313 | B2 * | 6/2005 | Houwen et al. .............. 435/7.2 |
| 2006/0269970 | A1 * | 11/2006 | Paul et al. .................. 435/7.21 |

OTHER PUBLICATIONS

Macey, "The Q-Prep System: Effects of the Apparent Expression of Leucocyte Cell Surface Antigens", Cytometry, 30(2):67-71 (Apr. 15, 1997).

Civin, C.I., et al., "Cell Surface Antigens on Human Marrow Cells: Dissection of Hematopoietic Development Using Monoclonal Antibodies and . . . ", Intl. J. Cell. Cloning, vol. 5, pp. 267-288 (1987).

Fujimoto, H., et al., "Flow cytometric method for enumeration and classification of reactive immature granulocyte populations", Cytometry 42, pp. 371-378 (2000).

Goossens, W., et al., "Preliminary data on the feasibility of bone marrow screening on the Sysmex XE-2100 automated hematology analyzer", Sysmex J. Intl., 11(2), pp. 70-73 (2001).

Stockert, J.C., "Cytochemistry of mast cells: new fluorescent methods selective for sulfated glycosaminoglycans", Acta. Histochem., 102, pp. 259-272 (2000).

Thomas, R.A., et al., "Combined Optical and Electronic Analysis of Cells with the AMAC Transducers", J. Histochem and Cytochem, vol. 25, No. 7, pp. 827-835 (1997).

Weiland, T., et al., "Evaluation of the Automated Immature Granulocyte Count (IG) on Sysmex XE-2100 Automated Haematology Analyzer vs . . . " Sysmex J. Intl., 12(2), pp. 63-70 (2002).

European Search Report in European Patent Application No. 05754002.3 (Apr. 25, 2008).

* cited by examiner

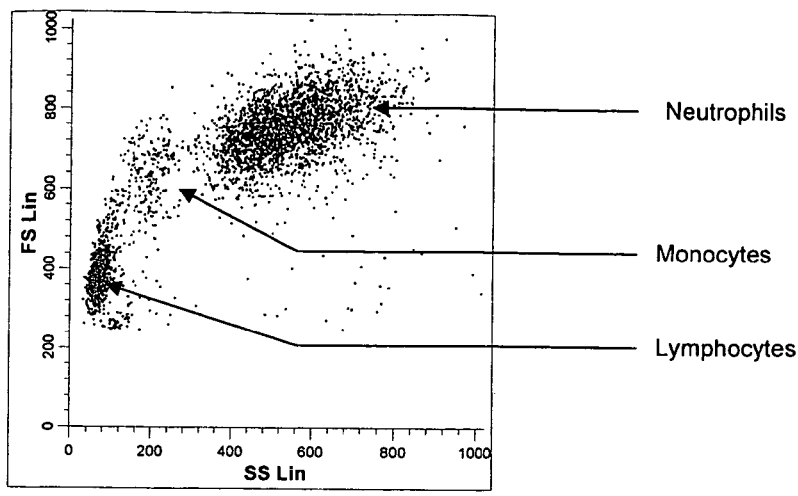
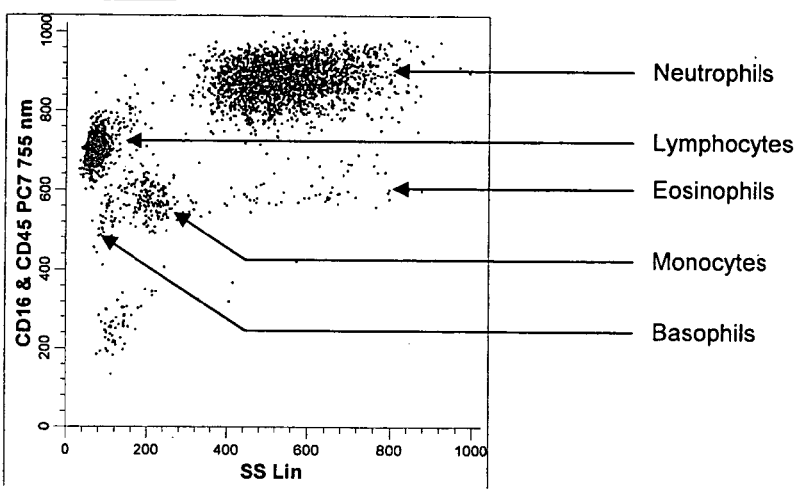
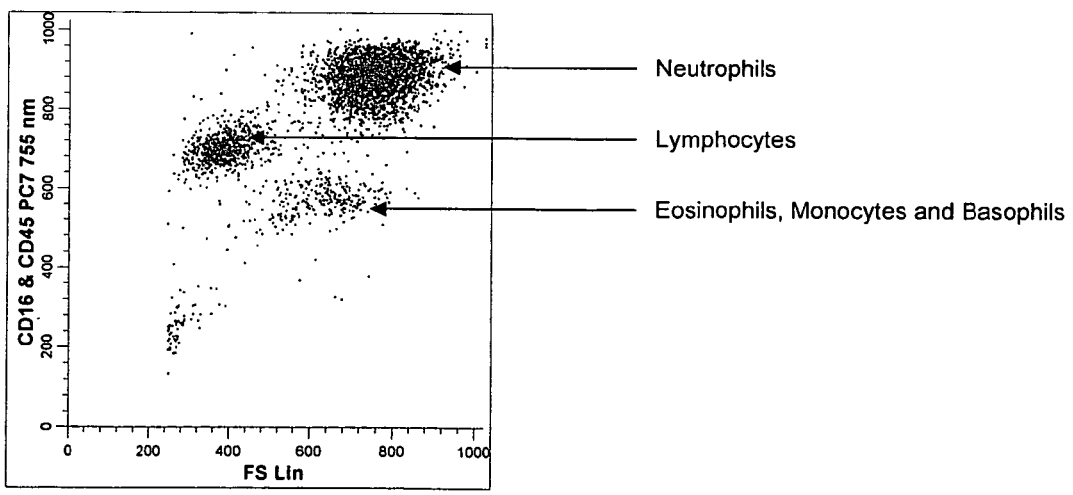

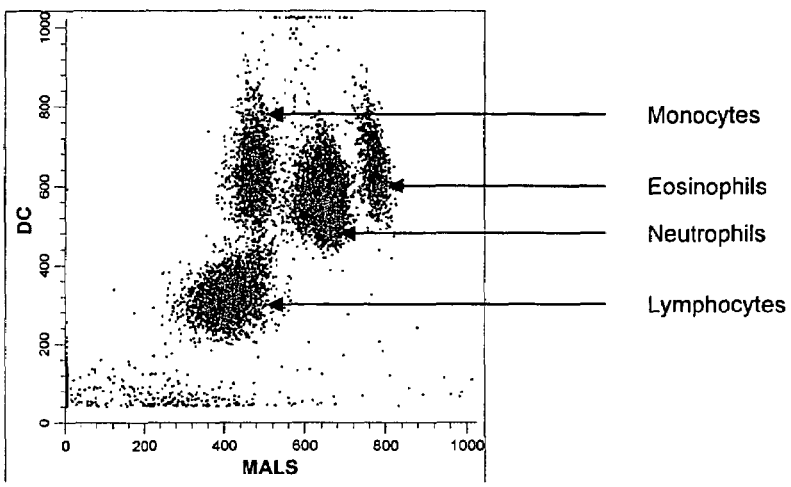
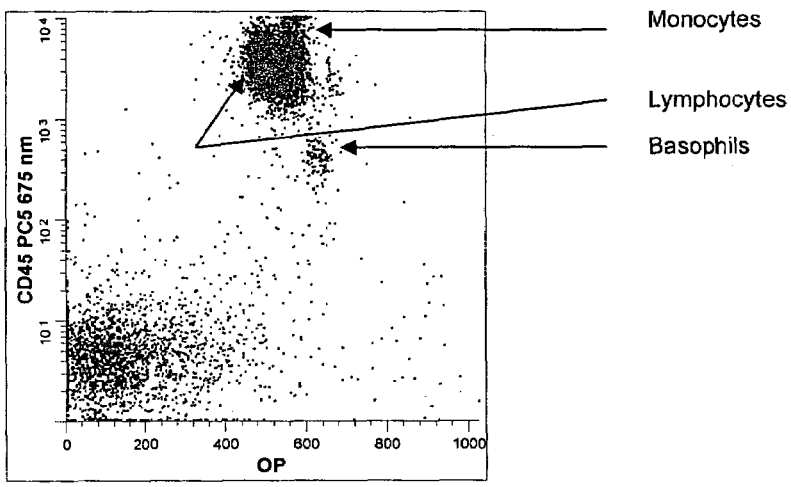
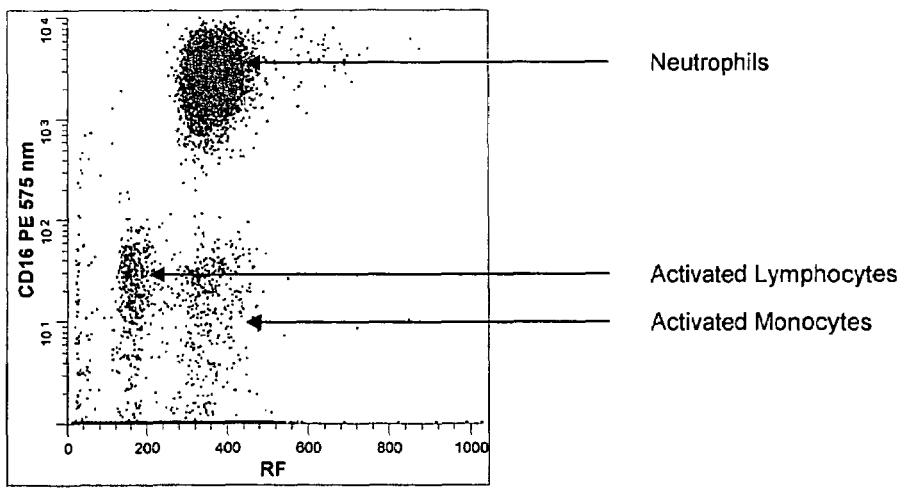

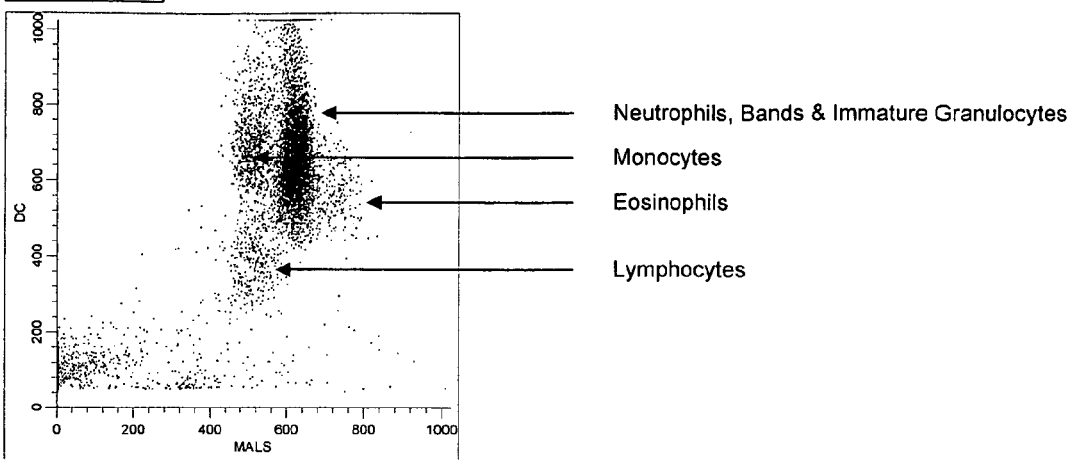
Figure 4A — Neutrophils, Bands & Immature Granulocytes; Monocytes; Eosinophils; Lymphocytes
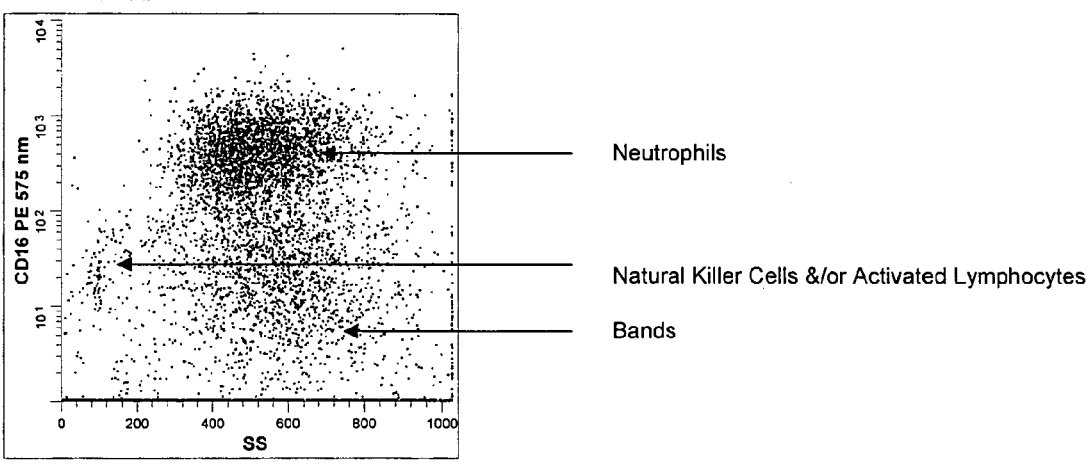
Figure 4B — Neutrophils; Natural Killer Cells &/or Activated Lymphocytes; Bands
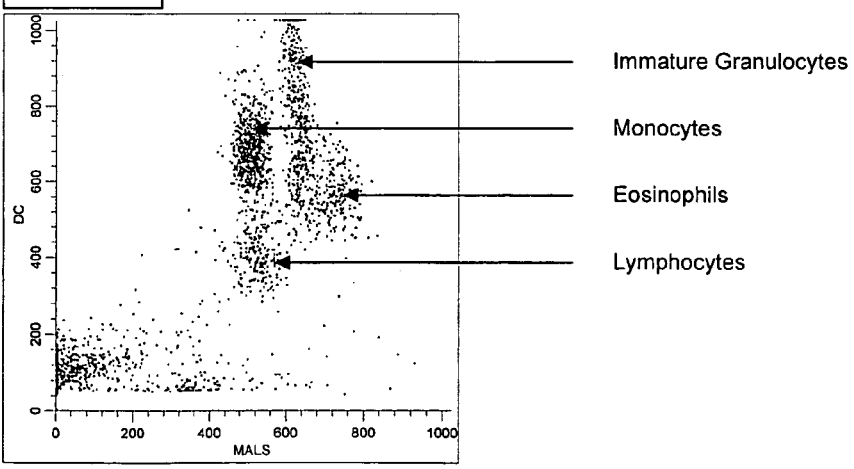
Figure 4C — Immature Granulocytes; Monocytes; Eosinophils; Lymphocytes

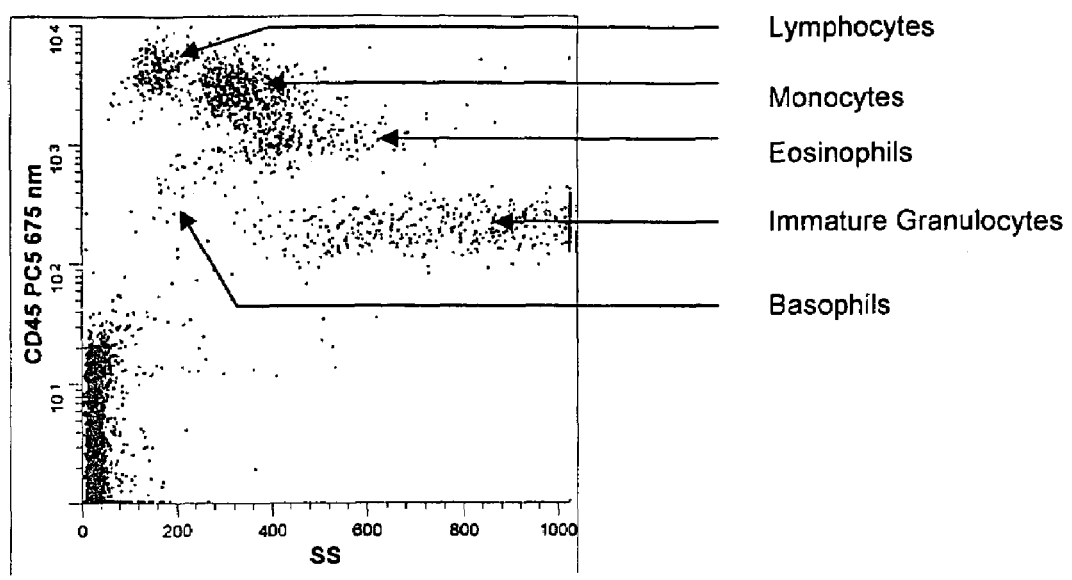

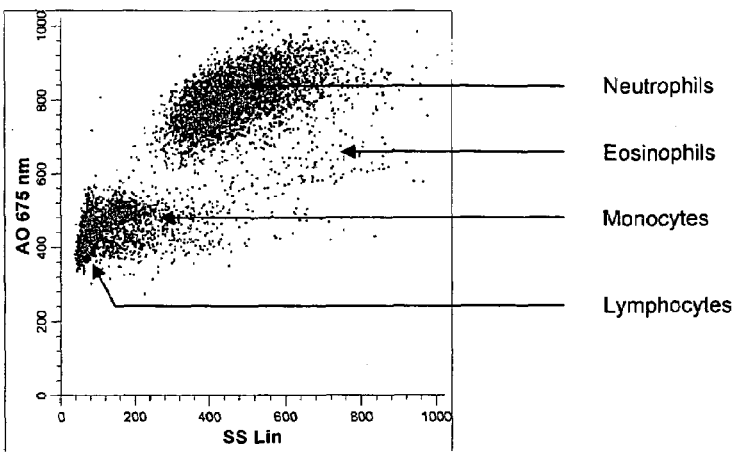
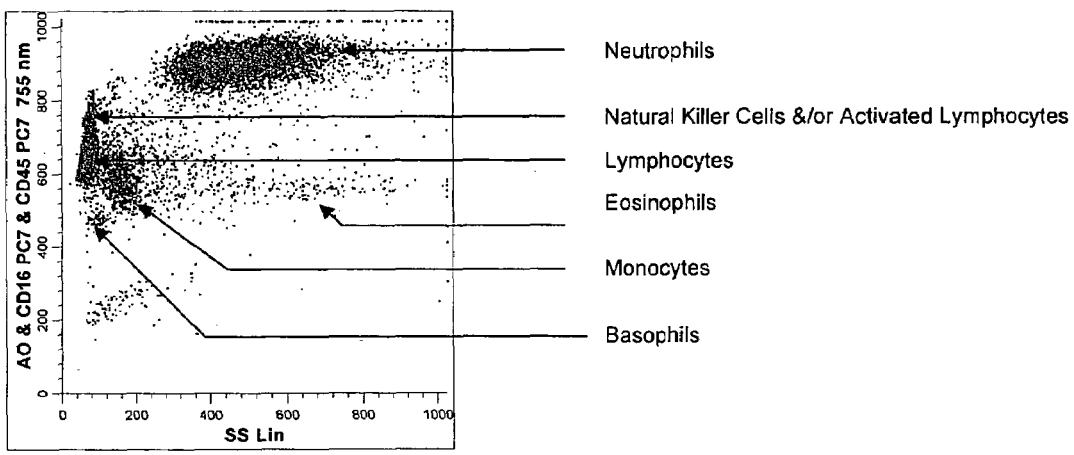
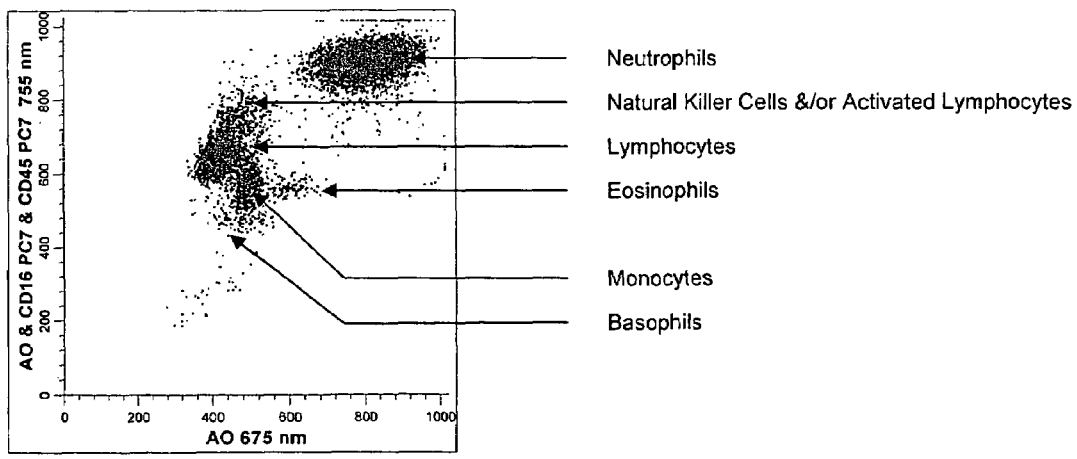

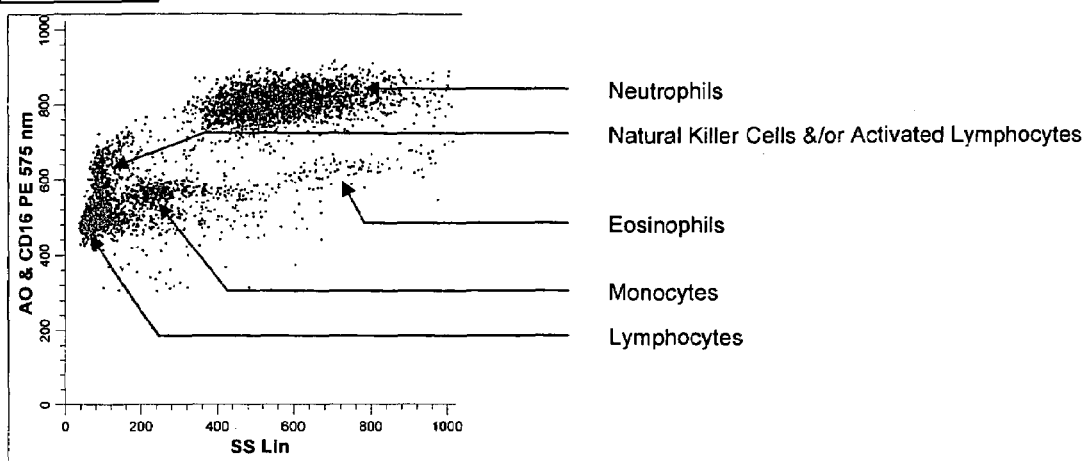
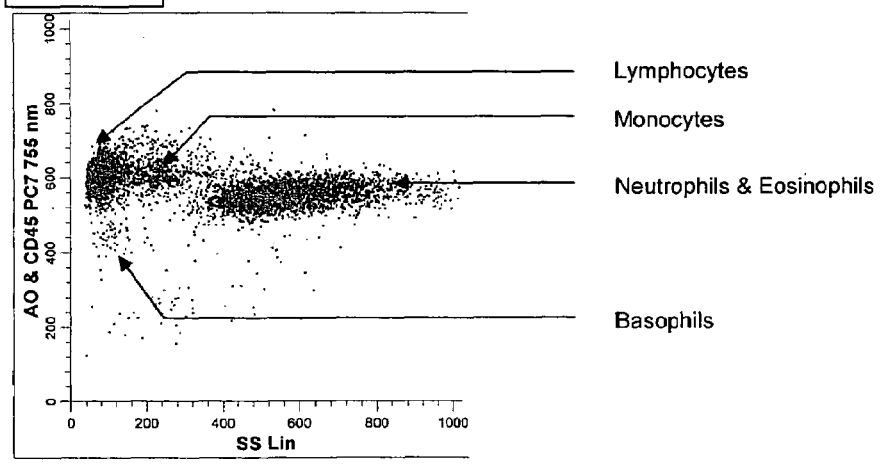

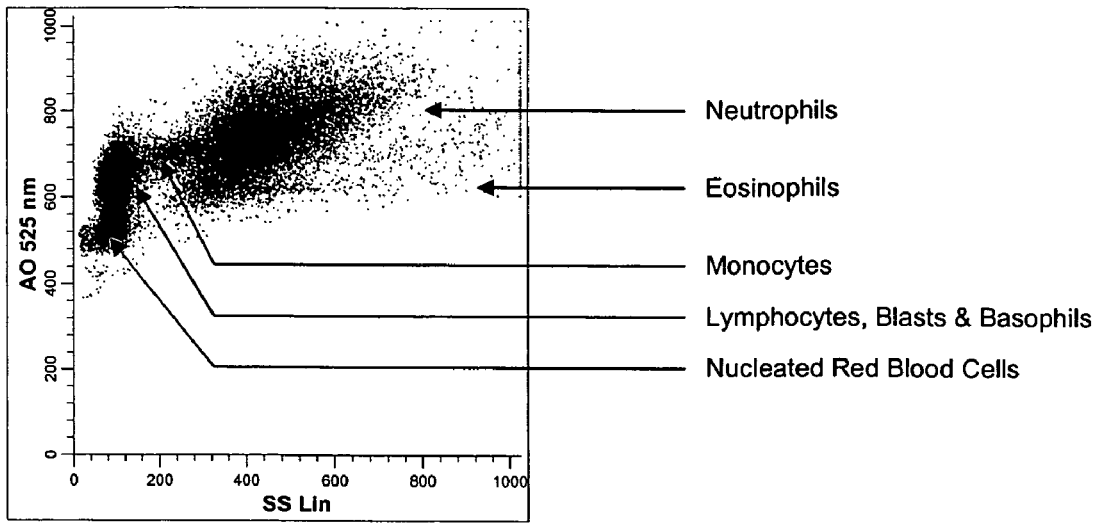
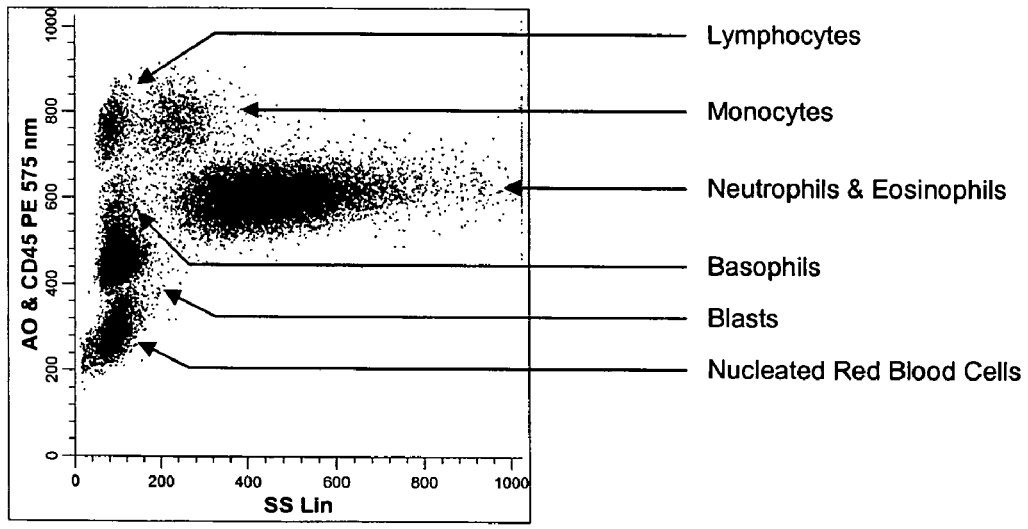

METHOD FOR A FULLY AUTOMATED MONOCLONAL ANTIBODY-BASED EXTENDED DIFFERENTIAL

CROSS REFERENCE TO RELATED APPLICATIONS

This application is a continuation-in-part of U.S. patent application Ser. No. 11/130,492, filed May 17, 2005, allowed which claims the benefit of the priority of U.S. Provisional Patent Application No. 60/573,167, filed May 21, 2004, now abandoned.

BACKGROUND OF THE INVENTION

Whole blood and peripheral blood samples from human subjects suffering from a variety of diseases can contain both blood cells or non-blood cells (e.g., tumor cells, bacteria, etc.) suspended in a liquid medium or plasma. The blood cells include red blood cells (erythrocytes or RBCs), white blood cells (leukocytes or WBCs), and platelets. Depending on the level of maturity of the cells, red cells are further classified into nucleated RBCs (NRBCs), reticulated RBCs (reticulocytes), and mature RBCs. Mature white cells fall into one of five different "normal" categories, namely, monocytes, lymphocytes, eosinophils, neutrophils and basophils. Each of the white cell subsets can be further classified into subclasses based on their respective level of maturity, activation, lineage, function, phenotype, or abnormality. Typically, only mature cells are present in detectable amounts in peripheral blood. The red cells in a normal human outnumber the total number of white cells by about 1000: 1. Platelets, which play a role in hemostasis, are of three general types, megakaryocytes, immature reticulated platelets and mature platelets.

The differentiation and enumeration of these various types of blood cells and platelets in a patient's peripheral blood, as well as the determination of certain parameters or characteristics thereof, permit diagnosis of a variety of hematological disorders or diseases. The absolute numbers, concentrations and relative percentages of the different types of blood cells are highly indicative of the presence or absence and/or stage of certain disease states.

Current commercially available, high throughput hematology flow analyzers provide a number of measured and mathematically derived cellular indices on red blood cells, platelets and white blood cells in peripheral blood specimens. The detection and enumeration of primarily mature cell types, as well as a determination of additional cell parameters, can be accomplished by using a commercially available hematology instrument. In automatically acquiring data on each cell type, most hematology instruments use at least two discrete cell-analyzing transducers. One or more of these transducers operate to acquire data useful in differentiating and enumerating the five different types of WBCs mentioned above. Another transducer is dedicated to counting and sizing of RBCs, WBCs and platelets in a precise volume of sample. The respective outputs of the multiple transducers are processed by a central processing unit to provide an integrated cell analysis report. The respective outputs of the several transducers are correlated to provide the five-part WBC differential information. Most current hematology systems identify normal blood cell populations by examining a combination of light scatter measurements or light scatter and electrical measurements collected in sequential analyses of the same reaction mixture (i.e., an aliquot of the same sample) or from analyses of different reaction mixtures of the same sample. Conventional hematology instruments, while capable of differentiating and enumerating the vast majority of cell types and subsets normally present in a peripheral blood sample, cannot readily differentiate multiple subsets of cells in a single sample, particularly those cells that are atypical or immature. The ability to provide relevant information beyond the total white blood cell count is directly related to the inclusion of multiple analytical parameters within hematology systems. Various configurations or combinations of electrical current impedance, conductivity, light scatter, absorbance, axial light loss and fluorescence have been used to determine the five-part differential, as well as to provide flagging information for the presence of atypical cell types by using different aliquots of the same sample.

An "extended differential" measurement includes the normal 5-part differential as well as the detection and enumeration of atypical cells (e.g., cells which are considered abnormal in relation to cells in healthy human blood) and immature cells. Due to the current limitations of commercially available hematology instruments, a skilled medical technologist must perform a microscopic examination (Manual Differential) in order to obtain an extended differential analysis. A blood-smear of a sample of interest produced manually on a glass microscope slide is stained with a dye to enable all cells, including the atypical or immature cells, to be visually differentiated from each other under a microscope.

Alternatively, some blood cell types of an extended differential measurement can be detected using a conventional flow cytometer. In such an instrument, a blood sample is prepared, e.g., by either (1) mixing the sample with fluorochrome-labeled monoclonal antibodies or the like which serve to selectively "tag" certain cells of interest, or (2) mixing the sample with a fluorescent stain adapted to selectively mark cells of interest, and passed through an optical flow cell. As each cell in the sample passes through the flow cell, it is irradiated with a beam of photons adapted to excite the fluorescent material associated with the cells of interest. Fluorescent light, emitted by each of the labeled cells, and light scattered by each cell are detected and used to differentiate the cells of interest from other cells in the sample.

Flow cytometers and hematology instruments have previously been integrated into a single automated laboratory system in which blood samples are automatically advanced along a track past these different instruments. As sample-containing vials pass each instrument, a blood sample is aspirated from each vial and analyzed by the instrument. Instrument systems combining discrete hematology and flow cytometry instruments are commercially available. The requirement to correlate the respective outputs of multiple transducers in order to report certain characteristics of a cell type or subset can, under certain circumstances, be problematic, in that it introduces uncertainty in the analytical results (U.S. Pat. Nos. 5,631,165 and 5,565,499; see, e.g., Thomas et al., J. Histochem. Cytochem., 25(7): 827-835 (1977)).

Fluorescence based flow cytometry has been used to determine leukocyte lineage and state of maturation. Traditional flow cytometric analysis of multiple qualitatively distinct antigenic determinants is usually performed by employing a distinct fluorochrome for each antibody utilized in the same analysis. Usually a series of analyses are performed in order to derive clinically relevant information. This requires a separate fluorescence detector, optics and electronics for each fluorochrome used and often the incorporation of more than one laser. See, e.g., C. I. Civen et al, 1987, *Internat'l. J Cell Cloning,* 5:267-288; U.S. Pat. No. 5,234,816; and U.S. Pat. No. 5,137,809.

Of the technologies discussed, fluorescence based measurements have the potential to provide greater advances in hematocellular analysis. Unlike the other aforementioned technologies that take advantage of the differences in the intrinsic physical properties of cells, fluorescence detection can examine the extrinsic properties of cells through the use of probes such as fluorescent dyes, histochemical stains, and fluorescent conjugated hybridization probes or monoclonal antibodies. Fluorescence measurements have proven beneficial by providing a high degree of sensitivity and specificity through the selection of appropriate reagents. Fluorescence based flow cytometry systems have been utilized for a number of years in research environments and more recently in clinical laboratories for performing immunodeficiency analyses, DNA cell cycle analyses, and leukemia/lymphoma immunophenotyping. More recently, fluorescence measurements have been introduced on routine hematology flow systems initially for the purpose of enumerating reticulated RBCs, followed by NRBC enumeration.

A fluorescence based immuno-platelet count has also recently been announced. Of the three fluorescence measurements that have been discussed, two (reticulocyte enumeration and immuno-platelet count) are either secondary or reflex mode measurements. The only measurement that occurs as part of the leukocyte differential cycle is NRBC enumeration. This analysis is performed utilizing a nucleic acid intercalating dye (propidium iodide) and light scatter to differentiate between intact WBCs, damaged WBCs and NRBCs.

Despite the application of these technologies, the currently available analytic systems suffer from common shortcomings, including difficulty in the performance of an accurate 5-part white blood cell differential in the presence of various atypical leukocyte populations or other abnormal conditions (cellular/non cellular) that interfere with performance of the 5-part differential. In addition, the conditions that permit the detection of, or flagging for, the presence of atypical cell types suffer from high false positive or high false negative rates. These shortcomings are unacceptable because they either result in an unnecessarily high manual review rate or the failure to detect clinically significant abnormalities.

There remains a need in the art for a simple, rapid, method for determining both a comprehensive five-part differential, as well as an extended leukocyte differential, in a single analysis on either a multiparametric high throughput hematology analyzer or a specialty hematology analyzer, and compositions facilitating such methods.

SUMMARY OF THE INVENTION

The need in the art is addressed by providing various embodiments of compositions and methods for hematology analysis which use unique combinations of fluorochrome-labeled antibodies and/or fluorescent dyes.

In one aspect, a composition or kit for differentially identifying cells in an instrument includes a fluorescent dye capable of staining cells, which has a dye emission spectrum; a first antibody that binds to an antigenic determinant that is differentially expressed on populations of blood cells, the antibody labeled with a fluorochrome having a first peak emission spectrum; and an optional additional antibody that binds to a second antigenic determinant that is differentially expressed on populations of blood cells, the antibody labeled with the same fluorochrome or a different fluorochrome having a second peak emission spectrum. The dye and fluorochromes labeling the antibodies of the composition are selected so that at least two spectra (i.e., the dye emission spectrum, the first peak emission spectrum and/or the second peak emission spectrum) overlap. The overlap forms a spectral emission that cannot be separated or resolved by optical or color compensation methods into the individual spectra or peak spectra of the two (or three) components. When utilizing the compositions described herein consisting of fluorescent dyes and fluorochrome labeled antibodies with overlapping spectra that cannot be separated or distinguished based upon optical or electronic compensation means, a new fluorescent footprint is established. This new fluorescent footprint is a result of the overlapping spectra and the combined cellular staining patterns of the dyes and fluorochrome labeled antibodies chosen for the composition. The new fluorescent footprint results in histogram patterns that are useful for the identification of additional cell populations or subtypes in hematological disease. A variety of such compositions are disclosed herein.

In another aspect, a composition comprises combinations of antibodies, which do not require the fluorescent dye described above, but rely on a combination of fluorochromes of overlapping peak emission spectra to permit use in hematological analysis. One embodiment of such a composition includes a first antibody that binds to an antigenic determinant that is differentially expressed on populations of blood cells, the antibody labeled with a fluorochrome having a first peak emission spectrum. The composition further includes a second antibody that binds to a second antigenic determinant that is differentially expressed on populations of blood cells. The second antibody is labeled with the same fluorochrome as on the first antibody or a different fluorochrome having a second peak emission spectrum that overlaps the first peak emission spectrum. The overlap forms a spectral emission that cannot be separated or resolved by optical or color compensation methods into the individual spectra or peak spectra of the two components. The new fluorescent footprint, i.e., the result of the overlapping spectra and the combined cellular staining patterns of the dyes and fluorochrome labeled antibodies chosen for the composition, results in histogram patterns that are useful for the identification of additional cell populations or subtypes in hematological disease. The composition can also include an optional additional antibody that binds to a third antigenic determinant that is differentially expressed on populations of blood cells. This optional antibody is labeled with a fluorochrome having a third peak emission spectrum that does not overlap the first peak emission spectrum.

In yet another aspect, a method for the enumeration of multiple cell populations in a biological sample is performed by mixing or reacting the sample, with one of the compositions described herein in a single reaction mixture. These compositions are further elucidated in the following detailed description. In one embodiment of the method, the single reaction mixture is contacted with an optional lytic reagent that differentially lyses non-nucleated red blood cells present in the sample. The resulting single reaction mixture is then passed through a sensing region in a cell analyzer. The sensing region in one embodiment may be a single flow aperture; and the cell analyzer may be a flow hematology analyzer. This sensing region measures the mixture for at least two of the same or different parameters selected from one or more channels of fluorescence, one or more optical parameters, one or more electrical parameters, and combinations thereof, preferably in a single step. Populations of cells in the sample are enumerated by analyzing at least two parameters for each of the cell populations. Use of a composition as above herein permits the enumeration of multiple hematologic cell populations in a biological sample. When utilizing the compositions described herein consisting of fluorescent dyes and fluorochrome labeled antibodies with overlapping spectra that cannot be separated or distinguished based upon optical or electronic compensation means, a new fluorescent footprint is established. This new fluorescent footprint is a result of the overlapping spectra and the combined cellular staining patterns of the dyes and fluorochrome labeled antibodies chosen for the composition. The new fluorescent footprint results in histogram patterns that are useful for the identification of additional cell populations or subtypes in hematological disease.

In one embodiment, for example, at least seven, and preferably more, cell populations are identifiable in a single biological sample.

Other aspects and advantages of various embodiments of the invention of the claims are disclosed in the following detailed description thereof.

BRIEF DESCRIPTION OF THE DRAWINGS

FIGS. 1A thru 1C are dual parameter histograms representing an embodiment is described in which a normal peripheral blood specimen was reacted with a first antibody labeled with a first fluorochrome having a first peak emission spectrum, the first antibody binding to an antigenic determinant that is differentially expressed on populations of leukocytes and non-leukocytes (CD45-PC7) and an additional antibody labeled with the same first fluorochrome having the same peak emission spectrum as the first antibody. The two identical fluorochromes overlap to form a non-compensatable spectral emission. The additional antibody binds to an antigenic determinant that is differentially expressed on populations of mature and immature granulocytes or myeloid cells (CD16-PC7). The reaction mixture was then contacted with a lytic system that differentially lyses non-nucleated red blood cells present in the sample and conserves the leukocyte population in the sample. The reaction was performed in the absence of a fluorescent dye.

FIG. 1A is a two parameter histogram displaying forward light scatter (FS) vs. side scatter (SS). At least three cellular populations can be identified and enumerated in this display: lymphocytes, monocytes and granulocytes (containing eosinophils and neutrophils).

FIG. 1B is a two parameter histogram displaying fluorescence of (anti-CD16-PC7 and anti-CD45-PC7) vs. side scatter. At least five cellular populations can be identified and enumerated in this display: lymphocytes, monocytes, basophils, eosinophils and neutrophils.

FIG. 1C is a two parameter histogram displaying fluorescence of (anti-CD16-PC7 and anti-CD45-PC7) vs. forward scatter. At least three cellular populations can be identified and enumerated in this display: lymphocytes, neutrophils and a third cluster containing eosinophils, monocytes and basophils.

FIG. 2A is a two parameter histogram displaying side scatter (SS) vs. CD45-PE fluorescence. At least four cellular populations are identified and enumerated in this display: lymphocytes, monocytes, basophils and a cluster of granulocytes containing eosinophils and neutrophils.

FIG. 2B is a two parameter histogram displaying fluorescence CD16-PC7 fluorescence vs. side scatter (SS). At least four cellular populations are identified and enumerated in this display: neutrophils, monocytes, eosinophils and a cluster containing natural killer cells and activated lymphocytes.

FIG. 2C is a two parameter histogram displaying fluorescence CD16-PC7 fluorescence vs. CD45-PE fluorescence. At least four cellular populations are identified and enumerated in this display: lymphocytes, neutrophils, a cluster containing eosinophils and monocytes and an additional cluster containing natural killer cells and activated lymphocytes.

FIGS. 3A thru 3C are dual parameter histograms obtained by performing a method described herein in which a normal peripheral blood specimen was reacted with a first antibody labeled with a first fluorochrome having a first peak emission spectrum, the first antibody binding to an antigenic determinant that is differentially expressed on populations of leukocytes and non-leukocytes (CD45-PC5). An additional antibody is labeled with an additional fluorochrome (CD16-PE), wherein the additional antibody binds to an antigenic determinant that is differentially expressed on populations of mature and immature granulocytes or myeloid cells. The additional fluorochrome has an additional peak emission spectrum distinguishable from the first peak emission spectrum. The reaction mixture was then contacted with a lytic system that differentially lyses non-nucleated red blood cells present in the sample and conserves the leukocyte population in the sample. The reaction was performed in the absence of a fluorescent dye.

FIG. 3A is a two parameter histogram displaying DC (Impedance) vs. Median Angle Light Scatter (MALS) which is a forward angle of light scatter from approximately 20 to 40 degrees. At least four cellular populations are identified and enumerated in this display: lymphocytes, monocytes, neutrophils and eosinophils.

FIG. 3B is a two parameter histogram displaying fluorescence of CD45-PC5 vs. Opacity (OP) where OP=Radio Frequency (RF)/Impedance (DC) following removal of the neutrophils and eosinophils by gating them out from histogram FIG. 3A. In this example at least three cellular populations are identified and enumerated: lymphocytes, monocytes and basophils.

FIG. 3C is a two parameter histogram displaying fluorescence of CD16-PE vs. RF. At least three cellular populations are identified and enumerated in this display: activated lymphocytes, activated monocytes and neutrophils.

FIGS. 4A thru 4D are dual parameter histograms obtained by performing a method described herein in which a peripheral blood specimen containing immature granulocytes and bands, was reacted with a first antibody labeled with a first fluorochrome having a first peak emission spectrum. The first antibody binds to an antigenic determinant that is differentially expressed on populations of leukocytes and non-leukocytes (CD45-PC5). An additional antibody is labeled with an additional fluorochrome (CD16-PE), wherein the additional antibody binds to an antigenic determinant that is differentially expressed on populations of mature and immature granulocytes or myeloid cells. The additional fluorochrome has an additional peak emission spectrum distinguishable from the first emission spectrum. The reaction mixture was then contacted with a lytic system that differentially lyses non-nucleated red blood cells present in the sample and conserves the leukocyte population in the sample. The reaction was performed in the absence of a fluorescent dye.

FIG. 4A is a two parameter histogram displaying DC (Impedance) vs. Median Angle Light Scatter (MALS). At least four cellular populations are identified and enumerated in this display: lymphocytes, monocytes, eosinophils and a cluster containing neutrophils, bands and immature granulocytes.

FIG. 4B is a two parameter histogram displaying fluorescence of CD16-PE vs. SS. In this example at least three cellular populations are identified and enumerated: neutrophils, bands and natural killer cells.

FIG. 4C is a two parameter histogram displaying DC vs. MALS following removal of the neutrophils and bands by gating them out from the histogram in FIG. 4B. At least four cellular populations are identified and enumerated in this display: lymphocytes, monocytes, eosinophils and immature granulocytes.

FIG. 4D is a two parameter histogram displaying fluorescence of CD45-PC5 vs. SS following removal of the neutrophils and bands by gating them out from the histogram in FIG. 4B. At least five cellular populations are identified and enumerated in this display: lymphocytes, monocytes, eosinophils, basophils and immature granulocytes.

FIGS. 5A thru 5C are dual parameter histograms obtained by performing a method described herein in which a normal peripheral blood specimen was reacted with a first antibody labeled with a first fluorochrome having a first peak emission spectrum. The first antibody binds to an antigenic determinant that is differentially expressed on populations of leukocytes and non-leukocytes (CD45-PC7). An additional antibody is labeled with the first fluorochrome (CD16-PC7) having the same peak emission spectrum as the first antibody. Thus, the antibodies have fluorochromes which overlap to form a non-compensatable spectral emission. The additional antibody binds to an antigenic determinant that is differentially expressed on populations of mature and immature granulocytes or myeloid cells. The reaction mixture was then contacted with a metachromatic, cell permeant, nucleic acid dye (Acridine Orange), which has an emission spectrum that either does not overlap or overlaps in a manner subject to separation by optics or color compensation with the peak emission spectrum of PC7. The mixture was analyzed without lysing the red blood cells present in the sample. The RBCs are not apparent in the histogram displays as they were set below the electronic threshold of the system in order to maximize the quantity of white blood cell events displayed.

FIG. 5A is a two parameter histogram displaying AO fluorescence at a wavelength of approximately 675 nm vs. SS. At least four cellular populations are identified and enumerated in this display: lymphocytes, monocytes, eosinophils and neutrophils.

FIG. 5B is a two parameter histogram displaying the fluorescence of AO, CD16-PC7 & CD45-PC7 at a wavelength of approximately 750 nm vs. SS. At least six cellular populations are identified and enumerated: lymphocytes, monocytes, neutrophils, eosinophils, basophils and natural killer cells.

FIG. 5C is a two parameter histogram displaying the fluorescence of AO, CD16-PC7 & CD45-PC7 at a wavelength of approximately 750 nm vs. the fluorescence of AO at a wavelength of approximately 675 nm. At least six cellular populations are identified and enumerated: lymphocytes, monocytes, neutrophils, eosinophils, basophils and natural killer cells.

FIGS. 6A and 6B are dual parameter histograms obtained by performing a method described herein in which a normal peripheral blood specimen was reacted with a first antibody labeled with a first fluorochrome having a first peak emission spectrum. The first antibody binds to an antigenic determinant that is differentially expressed on populations of leukocytes and non-leukocytes (CD45-PC7). An additional antibody labeled with an additional fluorochrome (CD16-PE) binds to an antigenic determinant that is differentially expressed on populations of mature and immature granulocytes or myeloid cells. This additional fluorochrome has an additional peak emission spectrum distinguishable from the first peak emission spectrum. Also used in this experiment is the metachromatic, cell permeant, nucleic acid dye (Acridine Orange) which has an emission spectrum that overlaps with the peak emission spectra of the fluorochrome PE. The sample was then passed through a single flow aperture in a flow hematology analyzer without lysing the red blood cells present in the sample. The overlap between AO and PE is non-compensatable, i.e., the emission pattern or spectra of PE cannot be compensated or resolved at its peak emission spectrum (~575 nm) from the emission spectra of AO. The spectral emission formed by the overlap of the dye emission spectrum and the fluorochrome's peak emission wavelength is non-compensatable. Upon fluorescent analysis, the new footprint results in a histogram pattern that is useful to identify additional cell populations or subtypes in hematological analysis. The RBCs are not apparent in the histogram displays as the displays were set below the electronic threshold of the system in order to maximize the quantity of white blood cell events displayed.

FIG. 6A is a two parameter histogram displaying AO and CD16-PE fluorescence at a wavelength of approximately 575 nm vs. SS. At least five cellular populations are identified and enumerated in this display: lymphocytes, monocytes, eosinophils, neutrophils and natural killer cells.

FIG. 6B is a two parameter histogram displaying of AO & CD45-PC7 fluorescence at a wavelength of approximately 750 nm vs. SS. At least four cellular populations are identified and enumerated: lymphocytes, monocytes, basophils, and a cluster of neutrophils and eosinophils.

FIG. 7A is a two parameter histogram displaying AO, CD16-PC7 & CD45-PC7 fluorescence at a wavelength of approximately 750 nm vs. SS. At least six cellular populations are identified and enumerated in this display: lymphocytes, monocytes, neutrophils, basophils, blasts and a cluster containing eosinophils and immature granulocytes.

FIG. 7B is a two parameter histogram displaying of AO fluorescence at a wavelength of approximately 675 nm vs. SS. At least four cellular populations are identified and enumerated: eosinophils, clusters containing lymphocytes and blasts, monocytes and blasts, and neutrophils and immature granulocytes.

FIG. 7C is a two parameter histogram displaying AO, CD16-PC7 & CD45-PC7 fluorescence at a wavelength of approximately 750 nm vs. SS following removal of the eosinophils by gating them out from FIG. 7B. At least six cellular populations are identified and enumerated in this display: lymphocytes, monocytes, neutrophils, basophils, blasts and immature granulocytes.

FIG. 8A is a two parameter histogram displaying AO fluorescence at a wavelength of approximately 525 nm vs. SS. At least four cellular populations are identified and enumerated in this display: lymphocytes, monocytes, neutrophils and eosinophils.

FIG. 8B is a two parameter histogram displaying of AO & CD16-PE fluorescence at a wavelength of approximately 575 nm vs. SS. At least six cellular populations are identified and enumerated: lymphocytes, monocytes, eosinophils, neutrophils, immature granulocytes and natural killer cells.

FIG. 8C is a two parameter histogram displaying AO fluorescence at a wavelength of approximately 525 nm vs. AO & CD45-PC7 fluorescence at a wavelength of approximately 750 nm following removal of the eosinophils by gating them out of FIG. 8A. At least five cellular populations are identified and enumerated in this display: nucleated red blood cells, neutrophils, immature granulocytes, basophils and a cluster containing lymphocytes and monocytes.

FIG. 9A is a two parameter histogram displaying AO fluorescence at a wavelength of approximately 525 nm vs. SS. At least four cellular populations are identified and enumerated in this display: lymphocytes, monocytes, neutrophils and eosinophils.

FIG. 9B is a two parameter histogram displaying of AO & CD16-PC7 fluorescence at a wavelength of approximately 750 nm vs. SS following removal of the eosinophils by gating them out from FIG. 9A. At least five cellular populations are identified and enumerated: lymphocytes, monocytes, neutrophils, immature granulocytes and natural killer cells.

FIG. 9C is a two parameter histogram displaying of AO & CD16-PC7 fluorescence at a wavelength of approximately 750 nm vs. AO & CD45-PE fluorescence at a wavelength of approximately 575 nm following removal of the eosinophils by gating them out from FIG. 9A. At least six cellular populations are identified and enumerated: lymphocytes, monocytes, neutrophils, immature granulocytes, nucleated red blood cells and natural killer cells.

FIG. 11A is a two parameter histogram displaying AO fluorescence at a wavelength of approximately 525 nm vs. SS generated from the experiment of Example 16 (using a single labeled antibody anti-CD45-PE, a fluorescent dye with overlapping spectrum with PE, and a lytic reagent). Using the new "footprint" formed as described herein, at least five cellular populations are identified and enumerated: neutrophils, eosinophils, monocytes, nucleated red blood cells, and a cluster containing lymphocytes, blasts and basophils.

FIG. 11B is a two parameter histogram displaying AO and CD45-PE fluorescence at a wavelength of approximately 575 nm vs. SS generated from the same experimental data. Using the new "footprint" formed as described herein, at least six cellular populations are identified and enumerated in this display: lymphocytes, monocytes, basophils, blasts, nucleated red blood cells and a cluster of granulocytes containing neutrophils and eosinophils.

DETAILED DESCRIPTION OF THE INVENTION

Figure 2A:
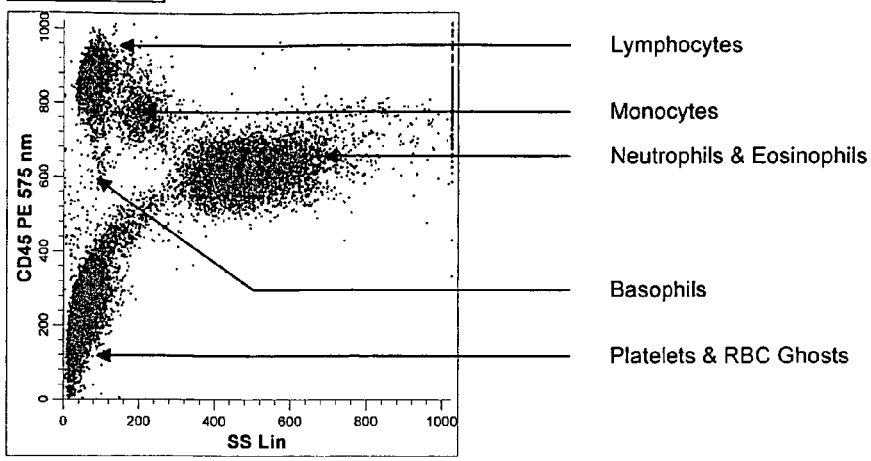
FIGS. 2A thru 2C are dual parameter histograms obtained by performing a method described herein in which a normal peripheral blood specimen was reacted with a first antibody labeled with a first fluorochrome having a first peak emission spectrum. The first antibody binds to an antigenic determinant that is differentially expressed on populations of leukocytes and non-leukocytes (CD45-PE). An additional antibody is labeled with an additional fluorochrome (CD16-PC7). The additional antibody binds to an antigenic determinant that is differentially expressed on populations of mature and immature granulocytes or myeloid cells. The fluorochrome on this antibody has an additional peak emission spectrum distinguishable from the first peak emission spectrum. The reaction mixture was then contacted with a lytic system that differentially lyses non-nucleated red blood cells present in the sample and conserves the leukocyte population in the sample. The reaction was performed without use of a fluorescent dye.

Methods of performing automated, rapid, extended leukocyte differential analyses for multiple cell types by providing for novel spectral patterns to identify additional cell populations are provided in embodiments described herein, e.g., preferably for the five normal leukocyte populations as well as at least one atypical population. As used herein, the term "composition" includes assemblies or kits or diagnostic products containing one or more of the below-identified reagents and components for use in such methods. Many embodiments of such compositions are described herein. The use of these compositions or assemblies or kits or products in hematological analysis methods enables the identification of a maximal number of cell populations while using a minimal number of components in the compositions. In an embodiment of the compositions and methods, at least two components, e.g., fluorochromes and/or fluorescent dyes have overlapping emission spectra that are not compensatable or resolvable at the peak emission spectrum of at least one of the components.

The method described herein for the enumeration of cell populations in a biological sample includes the following steps. In one embodiment, a single reaction mixture is formed by rapidly reacting the biological sample with an embodiment of a composition described in detail below.

Following preparation of the reaction mixture, the mixture is passed through a sensing region in a cell analyzer, e.g., a single flow aperture in a multiparametric high throughput flow hematology analyzer, in a single analytical step that measures the mixture for multiple parameters. These parameters may be the same or different and include one or more channels of fluorescence, one or more optical parameters, one or more electrical parameters, or combinations thereof. Thereafter, each cell population is identified and enumerated by using at least two of these parameters.

Another step of the method involves enumerating multiple populations of hematological cells (and optionally some atypical non-hematological cells) in the sample by analyzing at least two parameters for each different cell population. For example, in one embodiment, fluorescence analysis is combined with at least one simultaneously-measured electrical or optical measurement made on each individual cell as it passes through the transducer to identify a cell population. In this manner, an extended differential is obtained without the need for further separation of the lysed and unlysed fractions, if present, in the sample, or for correlation of different measurements made on different cells in the sample in different transducers.

Thus, the method described herein uses novel combinations of one or more labeled antibodies and/or a fluorescent dye and/or a lytic system to produce a remarkably efficient analysis. When utilizing the compositions or kits described herein consisting of fluorescent dyes and fluorochrome labeled antibodies with overlapping spectra that cannot be separated or distinguished based upon optical or electronic compensation means, a new fluorescent footprint is established. This new fluorescent footprint is a result of the overlapping spectra and the combined cellular staining patterns of the dyes and fluorochrome labeled antibodies chosen for the composition. The new fluorescent footprint results in histogram patterns that are useful for the identification of additional cell populations or subtypes in hematological disease with a minimum use of reagents and hardware.

The various embodiments of the methods of this invention and the compositions useful therein are described in detail below.

A. The Biological Sample

A biological sample as utilized herein is any mammalian cell-containing suspension that contains blood cells, preferably leukocytes. Such a specimen or sample can include hematological cells and non-hematological cells. Such a sample includes, without limitation, whole blood, peripheral blood, bone marrow aspirate, lymph node tissue, splenic tissue, cerebrospinal fluid, skin tissue, mucosal tissue, thoracentesis fluids, pleural fluids, and spinal fluid. Hematological (i.e., blood) cell populations are selected from the group consisting of monocytes, lymphocytes, neutrophils, eosinophils, basophils, myelocytes, metamyelocytes, promyelocytes, immature granulocytes, bands, blast cells, variant lymphocytes and atypical lymphocytes. Non-leukocyte hematological cell populations include red blood cells, reticulated red blood cells, nucleated red blood cells, platelets, reticulated platelets and megakaryocytes. In the blood, atypical cells include myelocytes, metamyelocytes, promyelocytes, immature granulocytes, band cells, blast cells, atypical lymphocytes, variant lymphocytes nucleated red blood cells, giant platelets, plasma cells, etc. Non-hematological cells include epithelial cells and endothelial cells, among others.

Preferably, the biological sample is human whole blood or peripheral blood sample containing the five "normal" leukocyte populations, which are monocytes, lymphocytes, neutrophils, eosinophils, and basophils, as well as possibly a number of atypical cell populations due to disease, reaction to an adverse environmental stimuli, e.g., a carcinogen, or a result of therapeutic treatment. Thus, suitable samples for analysis by these methods are human patient blood samples, which may likely contain both mature and immature leukocyte cells and non-leukocyte populations, as well as atypical cells. For example, in one embodiment, a sample contains blast cells. Another sample contains nucleated red blood cells. As another example, the sample contains immature granulocytes. As another example, the sample contains atypical lymphocytes. Other combinations of cells in abnormal samples may also be analyzed by the methods and compositions described herein.

By applying the method to such biological samples, information that contributes to the diagnosis, prognosis, staging and treatment of a variety of diseases can be made based on the "extended" or "5+ part" differential of the sample. Desirably, the methods described herein provide a 6-part differential, 7-part differential, 8-part differential, 9-part differential, or 10-part differential. A differential of more than 10 cell populations may also result from application of these methods, depending on the selection of the components of the single reaction mixture, as indicated above, and on the nature of the sample, e.g., blood, bone marrow, etc.

For use in a method as described herein, the biological sample volumes can be altered to fit the requirements of the system, but preferably range from about 10 µL to about 150 µL. More particularly, the sample volume can be at least about 20, 30, 40, 50, 60, 70, 80, 90, 100, 110, 120, 130 or 140 µL.

B. Components of the Methods and Compositions

In one embodiment, a composition or kit for differentially identifying cells in an instrument includes a fluorescent dye capable of staining cells, which has a dye emission spectrum; a first antibody that binds to an antigenic determinant that is differentially expressed on populations of blood cells, and an optional additional antibody that binds to a second antigenic determinant that is differentially expressed on populations of blood cells. The first antibody is labeled with a fluorochrome having a first peak emission spectrum. The optional additional antibody is labeled with either the same fluorochrome used to label the first antibody or a different fluorochrome having a second peak emission spectrum. The dye and fluorochromes labeling the antibodies of the composition are selected so that at least two spectra (i.e., the dye emission spectrum, the first peak emission spectrum and/or the second peak emission spectrum) overlap. The overlap forms a spectral emission pattern that cannot be separated or resolved by optical or color compensation methods into the individual spectra or peak spectra of the two (or three) components. These compositions may be in the form of assemblies or kits of the various components needed to perform the analytical methods described herein.

Thus, in one embodiment, the composition employs a single labeled antibody with a peak emission spectrum that overlaps the emission spectrum of a fluorescent dye, the overlap resulting in a non-compensatable spectral emission pattern. In another embodiment, the composition employs a fluorescent dye and two antibodies, each labeled with the same fluorochrome. The dye emission spectrum overlaps the peak emission spectrum of the fluorochromes labeling both antibodies. The overlap in emission spectra of the three components results in non-compensatable spectral patterns. In another embodiment, a composition of two labeled antibodies and a fluorescent dye is provided. The first peak emission spectrum of the fluorochrome labeling the first antibody overlaps the second peak emission spectrum of a different fluorochrome labeling the additional antibody, the overlap resulting in a non-compensatable spectral emission pattern. Neither the first nor second peak emission spectrum overlaps the dye emission spectrum. In another embodiment, the composition employs a fluorescent dye and two antibodies labeled with different fluorochromes. The dye emission spectrum overlaps the second peak emission spectrum of the additional antibody, the overlap resulting in a non-compensatable spectral emission pattern. Neither the dye emission spectrum nor the peak emission spectrum of the additional antibody overlaps the first peak emission spectrum of the fluorochrome labeling the first antibody. In another embodiment in which the compositions contains a fluorescent dye and two labeled antibodies, the dye emission spectrum overlaps both the first peak emission spectrum of the first antibody and the second peak emission spectrum of the second additional antibody, the overlaps resulting in one or more non-compensatable spectral emission patterns. Still other embodiments employ more than two antibodies, each antibody being labeled with the same fluorochrome as another antibody in the composition or with a different fluorochrome.

In another embodiment, multiple fluorochrome labeled antibodies with overlapping peak emission spectra, without the presence of a fluorescent dye are provided. The overlap results in a non-compensatable spectral emission pattern.

Also included in certain embodiments of the composition is a lytic system that can differentially lyse any red blood cells present in the sample and conserve the leukocyte and optional other nucleated populations in the sample. A differential lysing of the non-nucleated red blood cells in the reaction mixture and an optional quenching of the lysing reaction without altering the intrinsic or extrinsic properties of the nucleated cells (i.e., the WBC, mature RBC and platelets), permit retention of the nucleated cells for analysis.

Still other embodiments and the particular components of useful compositions are defined below.

1. Antibodies

Antibodies useful in the compositions and methods described herein, in conjunction with at least one other parametric measurement, provide the data required for a comprehensive extended cell differential in a single analytical process. The composition of reagents, which with the sample form a single reaction mixture, is designed so that one to three antibodies (directed at one to three qualitatively different antigenic determinants) may be utilized, optionally in concert with a fluorescent dye, without incorporating additional hardware (lasers, photomultiplier tubes, etc.) or more than one or two fluorochrome labels. It is also designed so that the individual antibody specificities within the composition, in conjunction with each other as well as the electrical or light scatter parameters, are able to provide the most information in a single analysis. In certain embodiments, compositions may employ more than three antibodies.

The term "antibody" as used herein is intended to encompass a polyclonal, monoclonal, synthetic or recombinant antibody of classes IgG, IgM, IgA, IgD and IgE. Antibody fragments are also useful, including without limitation, a Fab fragment, a Fab' fragment, a $F(ab')^2$ fragment or a Fc antibody fragment of one or more of the above intact antibodies. Similarly a single chain variable antibody fragment or a recombinant construct comprising a complementarity determining region (CDR) of an antibody may be employed as the antibodies useful in these methods. Further, a synthetic antibody or chimeric antibody or humanized antibody construct which shares sufficient CDRs to retain functionally equivalent binding characteristics of an antibody that binds a desired cell surface antigen may also be employed as the antibody of choice. Preferably highly specific antibodies are used in this method.

The individual antibodies for use within the reaction mixture each bind an antigenic determinant that is differentially expressed on populations of blood cells, and are chosen so that a particular combination in conjunction with light scatter and/or electrical parameters provides the desired extended differential information. For example, an antibody useful herein binds to an antigenic determinant that is differentially expressed on populations of leukocytes and non-leukocytes. Such an antigenic determinant may be completely absent from non-leukocytes and expressed only on leukocytes. Alternatively, such an antigenic determinant may be abundantly expressed on leukocytes and minimally expressed on non-leukocytes. Such an antibody thus permits the identification and differentiation of white blood cells from non-white blood cells, such as RBC, nucleated red blood cells or platelets. Still other embodiments employ more than one antibody that binds a different determinant on the same cell type or population. Therefore a combination of different antibodies that bind different determinants on the same cell type or population can be employed in place of a single antibody that binds one determinant on a cell population. In another embodiment, such an antibody (or combination of antibodies) is also capable of differentiating between mature leukocytes and immature leukocytes, based on differential expression of the antigenic determinant on leukocytes as they mature and age.

The most desirable antibody for this purpose is anti-CD45. The CD45 antigen is expressed by, or present on, most cells in the leukocyte populations, but is not expressed, or only minimally expressed, if at all, on other hematopoietic cells, such as erythrocytes and megakaryocytes. Differential expression can be displayed within leukocyte populations so that lymphocytes exhibit relatively high expression, whereas basophils exhibit relatively low expression. Expression of the CD45 antigen can also vary as a function of leukocyte maturation level. For example, blasts or stem cells express less CD45 antigen than their mature counterparts. Other antibodies with similar differential binding expression between white cells, non-white cells, and blasts, including anti-CD11a, anti-CD50, anti-CD18, anti-CD53, and anti-CD62L, among others, may be used as the first antibody in the compositions and methods described herein. Also useful are anti-CD235a to glycophorin A, anti-CD235b, anti-CD236, anti-CD236r, anti-CD239, anti-CD240, anti-CD241 and anti-CD242. Still other useful first antibodies may include anti-CD48, anti-CD82, anti-CD235c and anti-CD36.

Yet another antibody (or combination of antibodies) useful in the compositions and methods described herein binds to an antigenic determinant that is differentially expressed on populations of mature and immature granulocytes or myeloid cells. In certain embodiments, the composition contains two or more antibodies directed to antigenic determinants differentially expressed on mature and immature granulocytes or myeloid cells. For example, the distribution of the CD16 antigen is more restricted than CD45 with regard to leukocyte expression. The CD16 antigen has two isoforms: CD16α and CD16β. CD16β is expressed strongly on segmented neutrophils and bands and poorly or not at all on other cells in the myeloid series. In contrast, CD16α is expressed on a subset of leukocytes classified as natural killer (NK) cells, and on monocytes and macrophages. An antibody with broad expression for the CD16 epitope (CD16α and CD16β) is expressed strongly on segmented neutrophils, bands, NK cells, monocytes, and macrophages and expressed poorly or not at all on other cells in the myeloid series. Therefore, in conjunction with anti-CD45 and the additional optical and electrical parameters as selected by this method, the fluorescence of the one or more additional antibodies can identify and distinguish between differentiated myeloid cells, immature myeloid precursors, and stem cells or blasts. For example, because the CD16 antigen may be more conserved than the intrinsic properties of neutrophils, anti-CD16 can also be used to identify degranulated(ing) neutrophils, such as may occur due to age, therapeutic treatments and certain hypogranular conditions. In addition, NK cells can be identified. Other antibodies with useful binding properties that distinguish mature and immature myeloid cells for use as the one or more "additional" antibody in the method or composition include, without limitation, antibodies to CD11b, CD15, CD24, CD35, CD10, CD49d, CD64 and CD87. In one embodiment, a composition contains a combination of such antibodies, e.g., anti-CD16 and anti-CD87.

Additional antibodies which may be employed in the compositions and methods desirably bind to, or react specifically with, a different cell surface determinant on another WBC. For example, the CD19 antigen is a B lymphocyte-specific antigen that is expressed on cells of the B lineage from immature pre-B cells to mature B lymphocytes. It is the classical epitope that defines a B cell. The antibody anti-CD19 binds to immature and mature B cells and can be used to differentiate blasts of B cell origin, and permits the identification of such blast cells separately from other WBCs identified by the binding of CD45. Atypical WBCs include immature granulocytes, blasts, band cells and atypical lymphocytes. Antibodies that bind to cell determinants specific for such atypical cells include CD34, which binds to blasts and CD117, etc. The use of various combinations of these antibodies which bind antigenic determinants on blood cells permits further identification and distinction among the atypical cell types.

Optimal concentrations of antibodies used in the methods are defined based upon label selected, desired staining intensity, reaction kinetics and fluorescence carryover between fluorescence channels when using multiple antibodies with only one or two fluorochrome labels. Such concentrations may be determined by the person of skill in the art given the present teachings provided herein.

Desirably, the antibodies are designed for admixture into a single reaction mixture with a biological sample.

2. Fluorochromes

Preferably, each antibody selected for use in a composition or method described herein is associated with, or conjugated to, a fluorescent detectable label, called a fluorochrome. Fluorochromes are commonly used in diagnostic assays. Commonly used fluorochromes useful in labeling antibodies include the blue excitable fluorochromes, such as fluorescein isothiocyanate (FITC), Alexa 488, phycoerythrin (PE), PE-cyanin-5 (PC5), PE-cyanin-7 (PC7), PE-Texas Red (ECD) and Peridinin-chlorophyll-protein (PerCP) and the red excitable fluorochromes such as allophycocyanin (APC), Alexa 647, and APC-Cy7. Still other useful fluorochromes include the tandem dyes, PE-cyanin-5.5, and rhodamine. Alexa dyes, which are not tandem dyes, are also useful. Combinations of such labels, such as Texas Red and rhodamine, FITC+PE, FITC+PECy5, and PE+PECy7, among others may be used depending upon the type of laser employed in the flow cytometry apparatus. Other fluorochromes may be employed in the compositions and methods, and may include those excitable by radiation in the red, blue or green wavelengths or combinations thereof. Multiple fluorochromes may be independently selected from available fluorochromes. Alternatively, indirect labeling methods, such as biotin-avidin or primary and secondary labeled antibodies are useful to accomplish a similar effect.

All of these fluorescent dyes are commercially available, and their uses known to the art. Still other fluorescent dyes may be available from other sources or may be developed in the future. Such fluorescent dyes or fluorochromes are anticipated to be useful in these various methods in the same manner as is the exemplary fluorescent dye of the examples below.

Each fluorochrome has a characteristic "emission spectrum", of which a portion is a characteristic "peak emission spectrum". As used herein the term "emission spectrum" means generally the amount of electromagnetic radiation of each frequency a fluorochrome emits when it is excited. Generally, an emission spectrum is a range or profile formed by bands of certain frequency, usually measured in nanometers (i.e., wavelength). As used herein, the term "peak emission spectrum" means the most intense portion of the emission spectrum usually measured as maximum wavelength in nanometers. The peak emission spectrum for any given fluorochrome (and for most nucleic acid dyes with narrow emission spectra) is known and readily obtained from publications describing such fluorochromes, such as Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, IL, 1994/1995) Molecular Probes, and other similar texts or corresponding website, known to those of skill in the art and incorporated herein by reference. The peak emission spectrum for any given fluorochrome may also be obtained by performing a spectral scan using a spectrophotometer. See also, Tables 1 and 2 below for several examples of peak emission spectra of certain useful fluorochromes.

Each antibody used in the compositions and methods is associated or coupled with a selected fluorochrome. Methods for coupling or associating the label with the antibody are similarly conventional and known to those of skill in the art. Known methods of label attachment are described (see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, IL, 1994/1995); U.S. Pat. Nos. 6,692,968 and 5,164,311, among others. Thus, selection of the coupling methods is not limiting.

According to various embodiments of the methods and compositions described herein, the same or different fluorochromes are employed to label the antibody or antibodies. The identity of the fluorochromes depends upon whether the same fluorochrome or different fluorochromes are used to label two or more antibodies in the composition. If the same fluorochrome is used to label more than one antibody, each antibody will have "overlapping peak emission spectra". Such an overlap between identical fluorochromes is non-compensatable or non-separable. If two or more fluorochromes are used, one may select different fluorochromes, each with different peak emission spectra, which may be optionally overlapping peak emission spectra. In one embodiment, the peak emission spectra of the fluorochrome label on one antibody in the composition and method overlaps the peak emission spectra of the fluorochrome used to label another antibody to form a non-compensatable spectral emission.

In some embodiments, the peak emission spectra of the fluorochrome label(s) on the antibody(ies) used in the composition and method overlap to form a non-separable or non-compensatable spectral pattern. By the phrases "non-compensatable", "non-resolvable" or "non-separable" as applied to the spectral pattern formed by the overlapping emission spectra is meant that the spectral pattern formed by the overlap of the peak emission spectra of the fluorochromes labeling two antibodies cannot be separated or resolved into the component peak emission spectra. In one embodiment, the overlapping spectral pattern is not separable by current optics or color compensation methods (optical or electronic). Thus, the resulting non-compensatable spectral pattern is different from either of its component fluorochrome peak. The combination of this overlapping spectra and the combined cellular staining patterns of the dyes and fluorochrome labeled antibodies chosen for the composition results in histogram patterns that are useful for the identification of additional cell populations or subtypes in hematological disease. Selected coupled fluorochromes having overlapping peak emission spectra (in addition to use of the same fluorochrome on multiple antibodies) that form non-compensatable, non-separable spectral emission patterns are useful when present on two antibodies with different cellular distribution patterns and specificities to provide a new fluorescent cellular histogram pattern that is useful to identify additional cell populations or subtypes in hematological analysis. Suitable pairs of fluorochromes that form non-compensatable overlapping spectral emission patterns include, without limitation, the blue excitable pairs: FITC and Alexa 488, PE and Cy3, PC5 and PeCy5, PC5 and PerCP, PeCy5 and PerCP, PC7 and PeCy7, and the red excitable pair: APC and Alexa 647. Where two lasers of different color are used in the fluorescent analysis, suitable fluorochrome pairs include, without limitation, PC7 and APC-Cy7, and PeCy7 and APC-Cy7.

Alternatively, one may use different fluorochrome pairs which do not have overlapping peak emission spectra (referred to hereinafter as "non-overlapping" fluorochromes). For example, selected coupled fluorochromes for use (using one or two lasers) include PE (peak emission spectrum ~575 nm)+PECy5 (peak emission spectrum ~670 nm), PE+APC (peak emission spectrum~660 nm), FITC (peak emission spectrum ~520 nm)+PE, APC+PECy7 (peak emission spectrum ~770 nm), and PE+PECy7. All of these pairs of fluorochromes have non-overlapping peak emission spectra.

These lists of fluorochrome pairs that have non-compensatable overlapping emission spectra or compensatable overlapping emission spectra or emission spectra that do not overlap are representative only and do not attempt to include an exhaustive list. One of skill in the art should be readily able to select the appropriate fluorochrome combinations for use in the compositions and methods described herein in view of the additional teachings of this specification.

3. The Fluorescent Dye

In certain embodiments of the compositions and methods, a fluorescent dye is included. In one embodiment, the fluorescent dye has an emission spectrum that overlaps in a non-compensatable manner with at least one peak emission spectrum of a fluorochrome labeling at least one antibody employed in a composition or method described herein. In another embodiment, the dye emission spectrum either overlaps in a compensatable manner or does not overlap at all with the peak emission spectrum of the fluorochromes used in the compositions described herein. With reference to suitable fluorescent dyes, the term "emission spectrum " is defined in the same way as defined for fluorochromes above. Some dyes have broad emission spectra with a broad "peak" that extends for more than 200 nm. Other dyes have narrow peak emission spectra. Emission spectra for such dyes are also known in the art and published in a variety of well-known texts. See, e.g., Darzynkiewicz, Z and Kapuscinski J (1990). Acridine Orange: A versatile probe of nucleic acids and other cell constituents. In Flow Cytometry and Sorting, 2nd Edition, MR Melamed et al (Ed), Wiley-Liss Inc, New York, pp 291-314 Shapiro, Howard M. (2003) Practical Flow Cytometry $4^{th}$ edition, Wiley-Liss, Hoboken, NJ pp. 296-297.

The fluorescent dye is, in one embodiment, a nucleic acid dye. In another embodiment, the fluorescent dye is a cytophillic dye. In another embodiment, the fluorescent dye is a mitochondrial dye. In another embodiment, the fluorescent dye is an enzyme substrate dye. In one embodiment, the nucleic acid or dye is a cell-permeant dye. The dye may be metachromatic or non-metachromatic, or cell permeant or non-cell permeant. By the term "cell permeant" is meant to describe a dye that readily penetrates a cell membrane and stains the components of the cell without requiring the additional presence of a permeabilizing agent in the composition or reaction mixture. Typically, cell-permeant dyes are utilized to stain live cells or components of cells that have not been lysed.

In another embodiment, the fluorescent dye is a cell-impermeant dye, such as those cell-impermeant dyes within the red, green or blue-excited wavelength regions.

In a further embodiment, the fluorescent dye is an intercalating dye and/or a metachromatic dye. See, for example, the metachromatic dyes noted in Urban et al., 2000 Acta. Histochem. 102:259-272.

In a further embodiment, the fluorescent dye is a non-metachromatic dye. The term "non-metachromatic dye" is meant to describe a fluorescent dye that provides a single wavelength of excitation and/or emission when irradiated at a predetermined wavelength.

Suitable fluorescent dyes in certain embodiments of the methods and compositions described herein share a combination of the above characteristics. For example, Acridine Orange is a blue excitable, nucleic acid dye, which is metachromatic and cell permeant. Another useful dye is propidium iodide, which is a blue excitable, nucleic acid dye which is non-metachromatic and non-cell permeant. Another useful dye is Thiazole Orange, which is a non-metachromatic, cell permeant nucleic acid dye which excites in the blue ~488 nm wavelength. Fluorescein diacetate is another blue excitable dye which is not a nucleic acid dye, but a non-metachromatic, cell permeant, enzyme substrate dye. Rhodamine 123 is a blue-excitable, non-metachromatic cell permeant mitochondrial dye. The red excitable SYTO61 dye is a non-metachromatic, cell permeant, nucleic acid dye that excites at about ~633 nm. Similarly the red excitable dye TO-PRO-3 is a non metachromatic, non-cell permeant, nucleic acid dye.

Examples of other fluorescent dyes that may be utilized herein include, without limitation, the Pyronin Y dye, acridine dyes, the nonyl Acridine Orange dye (3,6-Bis-(dimethylamino)-10-nonylacridinium bromide, Molecular Probes, Eugene, Oreg.), and the Acridine Red dye (also commercially available as Pyronin B, Sigma-Aldrich Corp., St. Louis, Mo.); the Thiazole Orange dye (Becton Dickinson, Franklin Lakes, N.J.); Propidium Iodide (3,8-Diamino-5-(3-diethylamino-propyl)-6-phenyl-phenanthridinium iodide, Sigma-Aldrich Corp., St. Louis, Mo.); Ethidium Bromide (Sigma-Aldrich Corp., St. Louis, Mo.); Hexidium Iodide (Molecular Probes, Eugene, Oreg.); Dihydroethidium (Molecular Probes, Eugene, Oreg.); Ethidium Monoazide (Molecular Probes, Eugene, Oreg.), the Toluidine Blue dye (2-Amino-7-dimethylamino-3-methylphenothiazinium chloride, Sigma-Aldrich Corp., St. Louis, Mo.); the TOPRO-3 dye; the YOPRO-1 dye; the SYTO™ dye such as the SYTO™ 17 dye and the SYTO™ 59 dye through SYTO™ 64 dye; the TOTO™ dye such as the TOTO-1 dye and the TOTO-3 dye; the PO-PRO-3 dye; the YOYO™ dye such as the YOYO-1 dye; the BOBO™ dye; the POPO™ dye such as the POPO-3 dye; xanthene dyes; carbocyanine dyes; polymethine dyes including Astra Violet FR; Thiofalvine T; pseudoisocyanine; oxacarbocyanine dyes; azine dyes; diphenylmethane dyes; methine dyes; oxazine dyes; cyanine dyes; styryl dyes; and hydrosystilba-midine (Molecular Probes, Eugene, Oreg.). Many of these dyes, as well as others that can be utilized in the methods described herein, are commercially available from Molecular Probes Inc. (Eugene, Oreg.). See, U.S. Pat. No. 5,563,070, which is hereby incorporated by reference.

Examples of non-metachromatic dyes include, without limitation, the Neutral Red dye (3-Amino-7-dimethylamino-2-methylphenazine hydrochloride, Sigma-Aldrich Corp., St. Louis, Mo.), the Basic Orange™ 21 dye (Sigma-Aldrich Corp., St. Louis, Mo.), the DiOC dye (1,1'-Dimethyloxacarbocyanine, Molecular Probes, Eugene, Oreg.), the Pyronin™ Y dye (Polysciences, Inc., Warrington, Pa.), the Methylene Blue™ dye (3-Bis-(dimethylamino)-phenothiazin-5-ium chloride, Molecular Probes, Eugene, Oreg.), the Auramine™ O dye (4,4'-(Imidocarbonyl)-bis-(N,N,-dimethylaniline) monohydrochloride, Sigma-Aldrich Corp., St. Louis, Mo.), the LDS™ 751 dye (Quinolinium, 6-(Dimethylamino)-2-[4-[4-(dimethylamino)phenyl]-1,3-butadienyl]-2-ethyl perchlorate, Molecular Probes, Eugene, Oreg.), the Red series dyes, among others, and combinations thereof. See, e.g., various Beckman Coulter catalogs; The Handbook of Fluorescent Probes and Research Products, 6$^{th}$ Ed., R. P. Haugland, Molecular Probes, Eugene, Oreg. It should be noted that certain dyes can be metachromatic in some circumstances and non-metachromatic in others.

Examples of metachromatic dyes that can be utilized in the methods and compositions described herein include, without limitation, the xanthene dyes, carbocyanine dyes, polymethine dyes including Astra Violet F R, thiofalvine T, pseudoisocyanine, oxacarbocyanine dyes, acridine dyes, azine dyes, diphenylmethane dyes, methane dyes, oxazine dyes, cyanine dyes, and styryl dyes, among others. See, e.g., the metachromatic dyes noted in Urban et al., 2000 Acta. *Histochem.* 102:259-272.

In one embodiment of the compositions and methods, the fluorescent dye is Acridine Orange or nonyl Acridine Orange. In another embodiment, the dye is Thiazole Orange. In still another embodiment the dye is Propidium Iodide. In another embodiment, the dye is Acridine Red or Toluidine Blue dye.

In one embodiment the emission spectrum of the fluorescent dye overlaps one or more peak emission spectra of one or more fluorochromes used in these compositions and methods. That overlap forms a non-compensatable, non-separable spectral emission pattern that cannot be separated or resolved into its component spectra. The same definition applied above to the fluorochromes is applicable to this overlap between the dye emission spectrum and one or more fluorochrome peak emission spectra. Specifically, such non-compensatable spectral patterns cannot be separated by optics or color compensation, such as electronic color compensation. For example, the peak emission spectrum of the fluorochrome used to label at least one antibody in the composition, e.g., PE, overlaps the broad emission spectrum of the dye, Acridine Orange, and the overlap forms a spectral pattern that is non-compensatable.

The following tables below exemplify certain combinations of fluorescent dyes with fluorochromes useful for labeling antibodies with emission spectra or peak emission spectra that overlap to form non-compensatable (NC) spectral patterns. Also identified in the tables are combinations of dyes and fluorochromes which overlap, but which form patterns that are compensatable (C), i.e., separable into the component spectra or peak emission spectra by optics or color compensation. These combinations are representative only and do not attempt to include an exhaustive list. One of skill in the art should be readily able to select the appropriate non-compensatable overlapping dye/fluorochrome combinations for use in these compositions and methods in view of the additional teachings contained herein.

TABLE 1

| Blue | Blue excitable fluorochromes | | | | | |
|---|---|---|---|---|---|---|
| Excitable Dyes (488 nm) | FITC or Alexa 488 | PE or Cy3 | ECD (PE Texas Red) | PC5 or PeCy5 | PerCP | PC7 or PeCy7 |
| Emission Maximum: | ~520 nm | ~575 nm | ~620 nm | ~670 nm | ~670 nm | ~770 nm |
| Acridine Orange | NC | NC | NC | NC | NC | C |
| Propidium Iodide | C | NC | NC | C | C | C |
| Thiazole Orange | NC | C | C | C | C | C |
| Fluorescein Diacetate | NC | C | C | C | C | C |
| Rhodamine 123 | NC | C | C | C | C | C |

TABLE 2

| Red Excitable Dyes (633 nm) | Red excitable fluorochromes | |
|---|---|---|
| | APC or Alexa 647 | APC-Cy7 |
| Emission Maximum: | ~660 nm | ~770 nm |
| SYTO 61 | NC | C |
| TO-PRO-3 | NC | C |

Various combinations of dyes and fluorochromes that overlap and form non-compensatable spectral patterns may be used in these compositions and methods in the same manner as described for the Acridine Orange and PE which are used in the following examples.

4. The Lytic System

An optional lytic system can be employed to differentially lyse non-nucleated red blood cells in the biological sample, while conserving the desired intrinsic and extrinsic properties of the leukocyte populations, and conserving nucleated red blood cells (NRBC) and/or platelets as well. In one embodiment, the lytic system is a component of the method or composition in the absence of a fluorescent dye. In another embodiment, the lytic system is employed in the presence of a fluorescent dye, typically where the fluorescent dye is an impermeant dye, as described above. In some embodiments, a lytic system can include a single lytic reagent. In other embodiments, the lytic system includes two reagents, such as a lytic agent and a quench reagent. In some embodiments, a lytic system can include three reagents, a lytic agent, a quench reagent and a fixation reagent.

The lytic system can be a lytic reagent system including, but not limited to: Erythrolyse II (Beckman Coulter, Inc.), the lysing reagent disclosed in U.S. Pat. No. 5,882,933, incorporated by reference for the purposes of identifying the reagents. The lytic reagent can vary with the primary requirements being efficient lysis of the red blood cells, and the conservation of the antigenic determinants and desired electrical and optical properties on the WBCs and NRBCs and desired atypical cells.

In addition to employing a single reagent for lysis, the lytic systems useful in the compositions and methods described herein can include a second reagent, e.g., one that quenches or retards the effect of the lytic reagent during the remaining steps of the method, e.g., while the sample flows through the aperture in the transducer module. A useful lytic retarding agent may be selected depending upon the lysis agent and may likely be employed only where speed is an issue. An example of such a lytic retarding agent is Stabilyse™ reagent (Beckman Coulter, Inc.). The lytic retarding reagent can vary provided that the primary requirement of quenching of the lytic reaction as well as the conservation of the antigenic determinants and desired electrical and optical properties on the cells of interest are accomplished.

A conventional fixation reagent may also be employed depending upon the choice of lytic reagents or the preferred implementation of the method.

Other lytic systems are marketed commercially and include the Immunoprep™ system U.S. Pat. No. 5,030,554 (Beckman Coulter, Inc.), the Versalyse™ system, the FACSlyse™ system (Becton Dickenson), or an ammonium chloride system. These systems are useful in the methods and compositions described herein.

5. Other Optional Components

Sphering agents can optionally be included in the composition, reagents and methods described herein and can be readily selected by one of skill in the art. Desirably, the sphering reagent is a zwitterionic surfactant which isovolumetrically spheres the red blood cells and reticulocytes and increases permeability. Such reagents can also act as surfactants. Examples of sphering agents include the non-ionic surfactant Dodecyl-β-D-Maltoside, which suitably is in solution with a buffer such as phosphate buffered saline, zwitterionic agents such as alkyl amido betaine or an alkyl betaine such as lauroamidopropylbetaine, cocoamidopropylbetaine and cocoamidosulfobetaine, N-tetradecyl-N,N-dimethyl-3-ammonio-1-propanesulfonate, or N-dodecyl-N,N-dimethyl-3-ammonio-1-propanesulfonate. See, U.S. Pat. Nos. 5,633,167 and 5,438,003, which are hereby incorporated by reference. To effectively isovolumetrically sphere the reticulocytes and red blood cells within a blood sample, the, concentration of the sphering reagent in the composition is most preferably from about 3 μg/mL to about 50 μg/mL with a mOsm in the range of about 200 to about 400 mOsm, and preferably from about 250 mOsm to about 350 mOsm. However, one of skill in the art may readily adjust this concentration and osmolarity as needed or desired to isovolumetrically sphere the cells, taking into consideration the surfactant selected.

Some surfactants and detergents that also permeabilize cells may also be employed in the compositions described herein. Examples of surfactants include, without limitation, the anionic surfactant ammonium perfluoralkyl carboxylate (commercially available as Fluorad® FC-143 (3M Company, Minneapolis, Minn.)), sodium lauroyl myristoyl lactylate (commercially available as Pationic® 138C (R.I.T.A. Corp, Woodstock, Ill.)), or from the non-ionic surfactants Dodecyl-α-D-maltoside, N,N-bis[3-D-glucon-amidopropyl] cholamide, polyoxypropylene-polyoxyethylene block copolymer, N-tetradecyl-α-D-maltoside, Daconyl-N-methyl-glucamide, n-Dodecyl-α-D-glucopyranoside, n-Decyl-α-D-glucopyranoside, polyethylene glycol ester of stearic acid, ethoxylated cocomonoglyceride, octyphenoxypoly (ethyleneoxy) ethanol, ethoxylated octylphenol, and linear alcohol, or, from among the cationic surfactants, coco hydroxyethyl imidazoline, lauryltrimethylammonium chloride, decyltrimethylammonium bromide, octyltrimethylammonium bromide, or from among the zwitterionic surfactants lauramidopropyl betaine, N-tetradecyl-N,N-dimethyl-3-ammonio-1-propanesulfonate, N-dodecyl-N,N-dimethyl-3-ammonio-1-propanesulfonate, cocoamidopropylbetaine, cocoamidosulfobetaine, N-dodecyl-N,N-dimethyl-3-ammonio-1-propanesulfonate, N-tetradecyl-N,N-dimethyl-3-ammonio-1-propanesulfonate. Examples of detergents include, without limitation, non-ionic detergents.

Other cell permeabilizing agents are also optionally included in various embodiments of the compositions to permit cell impermeant dyes to permeate the cell membrane. Desirably, these components are used at a concentration between about 0 to about 1% of the total composition.

An embodiment of a composition may further contain other components, such as buffers. Suitable buffers include those that maintain the pH of the composition in the range of about 6 to about 9. Desirably, a pH in the range of about 7 to about 7.5 is maintained in the composition. Additionally, such buffers may also be used to adjust the concentration of one or more of the components of the composition. Examples of buffers that can be utilized in the methods and compositions described herein include, without limitation, phosphate buffered saline or isotonic saline, such as ISOTON II, Coulter Corporation, Miami, Fla., or the like. See, U.S. Pat. No. 3,962,125, which is hereby incorporated by reference. Selection of an appropriate buffer is not a limitation of the methods and compositions taught herein.

Preservatives can also be added to the compositions and may be selected from, but not limited to, 5-Chloro-2-methyl-4-isothiazolin-3-one, and 2-methyl-4-isothiazolin-3-one (such preservatives may be purchased commercially, e.g., as ProClin 300 or ProClin 150).

One of skill in the art would be able to select further reagents that can be utilized in the compositions for use in the various methods described herein.

6. Specific Embodiments

The compositions are typically prepared in an appropriate manner. In one embodiment, all of the components of the reaction mixture other than the sample itself may be assembled to form a kit.

In one embodiment, the composition or kit contains a fluorescent dye capable of staining cells, which has a characteristic dye emission spectrum and a "first" antibody that binds to an antigenic determinant that is differentially expressed on populations of blood cells in the sample. In one embodiment, the antigenic determinant is differentially expressed on populations of leukocytes and non-leukocytes. In another embodiment, the antigenic determinant is differentially expressed on populations of mature and immature granulocytes or myeloid cells. Still other antigenic determinants may be selected by one of skill in the art, as described above. This "first" antibody is labeled with a "first" fluorochrome having a characteristic "first" peak emission spectrum. In this embodiment in which only a single antibody is present, the emission spectrum of the dye overlaps the peak emission spectrum of the "first" fluorochrome, resulting in a non-compensatable spectral pattern. An example of such an embodiment is described in detail in Example 15 below.

In another embodiment of the method, the reaction mixture contains the "first" antibody, the fluorescent dye, and at least one additional antibody. The at least one additional antibody binds a different antigenic determinant that is differentially expressed on populations of blood cells. However, the antigenic determinant bound by the additional antibody is distinct from that of the first antibody in the composition. In one particular embodiment employing two antibodies and a fluorescent dye, the first antibody binds an antigenic determinant that is differentially expressed on populations of leukocytes and non-leukocytes and the second antibody binds an antigenic determinant that differentially expressed on populations of mature and immature granulocytes or myeloid cells.

In one such embodiment, the additional antibody is labeled with the same "first" fluorochrome, and thereby the first labeled antibody and additional labeled antibody have overlapping peak emission spectra, which are non-compensatable. In one embodiment, these peak emission spectra do not overlap the dye emission spectrum. In another embodiment, these peak emission spectra do overlap the dye emission spectrum, preferably a non-compensatable spectral pattern.

In another composition containing the first antibody, the dye and the additional antibody, the additional antibody is labeled with a fluorochrome that is different from the "first" fluorochrome, but that has a "second" peak emission spectrum. In one particular embodiment of this composition, only the first fluorochrome peak emission spectrum overlaps the dye emission spectrum, preferably forming a non-compensatable spectral pattern. In a second such embodiment, only the second fluorochrome peak emission spectrum overlaps the dye emission spectrum preferably forming a non-compensatable spectral pattern. In a third such embodiment, the first and second peak emission spectra overlap, preferably forming a non-compensatable spectral pattern., but do not overlap the dye emission spectrum.

In a fourth such embodiment, all three emission spectra overlap, preferably forming a non-compensatable spectral pattern. In still other embodiments of all such compositions, wherever there is an emission spectra overlap, the overlap preferably forms a non-compensatable spectral pattern.

In still other embodiments, a combination of more than one "additional" antibody is employed. The antibodies may be individually labeled with the same fluorochromes as used on the other antibodies in the composition, or with fluorochromes that have overlapping peak emission spectra with those fluorochromes labeling other antibodies of the composition and/or with the dye emission spectrum, or with fluorochromes that do not overlap the peak emission spectra of other fluorochromes or the dye emission spectrum in the composition.

Desirably, the compositions and methods employ only 1 to 3 antibodies (i.e., 0, 1 or 2 "additional" antibodies). However, other embodiments may employ more than 3 antibodies. Various embodiments of this aspect are illustrated in the Examples below.

Still other embodiments employ mixtures of antibodies with or without the presence of a fluorescent dye. For example, one such composition or kit contains a first antibody labeled with a fluorochrome having a first peak emission spectrum. The first antibody binds to an antigenic determinant that is differentially expressed on populations of leukocytes and non-leukocytes in a sample. The composition also contains at least one additional antibody. In one embodiment, the additional antibody binds to an antigenic determinant that is differentially expressed on populations of mature and immature granulocytes or myeloid cells and is labeled with the same fluorochrome having the first peak emission spectrum. In another embodiment the additional antibody binds to an antigenic determinant that is differentially expressed on populations of mature and immature granulocytes or myeloid cells and is labeled with a "third" fluorochrome having an emission spectrum that overlaps with the first peak emission spectrum. In another embodiment, the additional antibody that to an antigenic determinant that is differentially expressed on populations of mature and immature granulocytes or myeloid cells, and is labeled with a fluorochrome having a "third" emission spectrum that does not overlap with the first peak emission spectrum. In any of these embodiments, a fluorescent dye is present which has a dye emission spectrum that overlaps with the peak emission spectrum of at least one of the fluorochrome-labeled antibodies in the composition. At least one of the above-mentioned overlaps forms a non-compensatable spectral emission pattern. An optional lytic system that differentially lyses non-nucleated RBCs in the sample and conserves the leukocyte populations in the sample may also be included in this composition or kit.

One exemplary composition contains a first antibody meeting the description above and labeled with a first fluorochrome, e.g., anti-CD45-PECy7; a second antibody meeting the "additional antibody" description above and labeled with the same, i.e., peak emission spectrum-overlapping first fluorochrome, e.g., anti-CD16-PECy7; and a fluorescent dye, e.g., Acridine Orange. The peak emission spectra of the two antibodies overlap in a non-compensating manner because the fluorochromes are the same. Neither antibody peak emission spectra overlaps with the peak emission spectrum of Acridine Orange. See Example 5.

In another embodiment, a composition or kit contains a first antibody that binds to an antigenic determinant that is differentially expressed on populations of blood cells, which "first" antibody is labeled with a fluorochrome having a first peak emission spectrum, e.g., anti-CD45-PECy7. The composition also contains a second antibody meeting the "additional antibody" description above and labeled with a first fluorochrome, e.g., anti-CD16-PECy7; and a lytic system containing a lysing and quenching reagent. The peak emission spectra of the two antibodies overlap in a non-compensating manner because the fluorochromes are the same. A composition containing these components is designed for admixture into a single reaction mixture with a biological sample, the mixture permitting the enumeration of five to eight or more hematologic cell populations in the sample. An example of this type of composition, which contains no fluorescent dye, but does employ an optional lytic system, is demonstrated in Example 1 below.

In yet another embodiment, a composition contains a first antibody meeting the description above and labeled with a first fluorochrome, e.g., anti-CD45-PECy7; a second antibody meeting the "additional antibody" description above and labeled with a first fluorochrome, e.g., anti-CD16-PECy7, so that the two antibodies have non-compensatable overlapping peak emission spectra; a lytic system containing a lysing and quenching reagent, and a fluorescent dye, e.g., Acridine Orange, having a dye emission spectrum which is not overlapped by the peak emission spectra of the fluorochromes. Similar kit components may be included, as described above. See Example 7.

In another embodiment a composition contains a first antibody meeting the description above and labeled with a first fluorochrome, e.g., anti-CD45-PECy7 having a "first" peak emission spectrum; a second antibody meeting the "additional antibody" description above and labeled with a fluorochrome with a different "second" peak emission spectrum, e.g., anti-CD16-PE; and a fluorescent dye, e.g., Acridine Orange, having a dye emission spectrum that overlaps the "second" peak emission spectrum. This overlap results in a non-compensatable spectral pattern. This composition, if in the form of a kit may also contain suitable packaging, glassware or container components and instructions for carrying out a method described herein, among other items conventional to a kit. See Example 6.

In still another embodiment, a composition contains a first antibody meeting the description above and labeled with a first fluorochrome, e.g., anti-CD45-PECy7; a second antibody, meeting the "additional antibody" description above and labeled with a second fluorochrome, e.g., anti-CD16-FITC; and a lytic system containing a lysing and quenching reagent. Similar kit components may be included, as described above.

In yet another embodiment, a composition contains a first antibody meeting the description above and labeled with a first fluorochrome, e.g., anti-CD45-PECy7; a second antibody, meeting the "additional antibody" description above and labeled with a second fluorochrome, e.g., anti-CD16-PE; a lytic system containing a lysing and quenching reagent, and a fluorescent dye, e.g., Acridine Orange. The PE and AO emission spectra overlap to form a non-compensatable spectral pattern. Similar kit components may be included, as described above. See Example 8.

Still another aspect of this composition or method employs yet another additional antibody that binds to an antigenic determinant that is differentially expressed on populations of blood cells, which determinant is distinct from that of any another antibody in the composition. This additional antibody is labeled with a fluorochrome having a second peak emission spectrum that does not overlap the first peak emission spectrum. See, e.g., Examples 2-4. In yet another aspect, a mixture of these variously described antibodies is employed in the composition or method, without the fluorescent dye.

Preferably, in compositions without the fluorescent dye, one of the antibodies binds to an antigenic determinant that is differentially expressed on populations of leukocytes and non-leukocytes and another of the antibodies binds to an antigenic determinant that is differentially expressed on populations of mature and immature granulocytes or myeloid cells. Examples of such antibodies and antigenic determinants are described above in the paragraphs on antibodies and in Examples 1-4. The lytic system of 1 to 3 reagents, as described above, is also optional for these embodiments.

A specific embodiment of such a composition includes a first antibody labeled with a fluorochrome having a first peak emission spectrum, the first antibody binding to an antigenic determinant that is differentially expressed on populations of leukocytes and non-leukocytes in a sample. At least one additional antibody binds to an antigenic determinant that is differentially expressed on populations of mature and immature granulocytes or myeloid cells. The additional antibody is labeled with the same fluorochrome having the first peak emission spectrum; or with a fluorochrome having a second peak emission spectrum that does not overlap the first peak emission spectrum; or with a fluorochrome having a second peak emission spectrum that overlaps with the first peak emission spectrum, preferably to form a non-compensatable spectral pattern. In a similar embodiment a lytic system that differentially lyses non-nucleated red blood cells present in the sample and conserves the leukocyte populations in the sample is also employed.

In yet another embodiment, a composition or kit consists of only two antibodies meeting the definitions below, and an optional lytic system. No fluorescent dye is used. One antibody binds to an antigenic determinant that is differentially expressed on populations of blood cells, and is labeled with a fluorochrome having a first peak emission spectrum. The second antibody binds to an antigenic determinant that is differentially expressed on populations of blood cells, wherein the determinant is distinct from that of the first antibody. The additional antibody is labeled with a fluorochrome having a second peak emission spectrum that does not overlap with the first peak emission spectrum. In one embodiment, the specific antibodies selected for this method enable the composition to identify at least seven hematologic cell populations in a sample. The composition may also employ a lytic system that differentially lyses non-nucleated red blood cells present in the sample and conserves the leukocyte populations in the sample. Examples of this aspect are demonstrated in Examples 2 through 4 below.

Thus, in some embodiments, the first antibody or antibodies is/are selected from among anti-CD45, anti-CD11a, anti-CD50, anti-CD18, anti-CD53, anti-CD62L or combinations thereof. The second antibody or antibodies is/are selected from one or a combination of an anti-CD16 capable of binding both antigens CD16α and CD16β, anti-CD16α, anti-CD16β, anti-CD11b, anti-CD15, anti-CD35 anti-CD24, anti-CD10, anti-CD49d, anti-CD64, and anti-CD87. In embodiments in which the fluorochromes on each antibody do not have overlapping peak emission spectra, such fluorochromes are preferably selected from among the pairs previously identified listed above. In embodiments in which the fluorochromes on each antibody do have peak emission spectra which overlap in a non-compensatable, non-separable manner, such fluorochromes may be the same fluorochromes or the overlapping pairs previously identified above.

In some embodiments, the above-described compositions are in the form of a kit containing the combination of components described above generally or in the specified embodiments. These embodiments contain any of the additional components described above, including more than one additional antibody with the same or different, overlapping or non-overlapping fluorochrome labels, a sphering agent or other components mentioned above. In certain embodiment, the compositions in the form of a kit also contain suitable packaging, glassware or container components, reagents for labeling the antibodies with the fluorochromes, and instructions for carrying out the various methods described herein, among other items conventional to a kit. A composition containing these components is designed for admixture into a single reaction mixture with a biological sample, the mixture permitting the enumeration of at least five to eight or more hematologic cell populations in the sample.

C. The Multiparametric High Throughput Hematology Methods

Methods for the rapid identification and analysis of cell populations, both normal and atypical, in a biological sample are performed using the above-defined compositions and the following steps. Preferably, the methods are fully automated, although several steps may be performed manually, if necessary. The methods for the enumeration of cell populations in a biological sample generally employ reacting in a single reaction mixture comprising the sample and one of the compositions as described herein. In one embodiment, the compositions may be added to the sample by first adding only the antibody components, followed by other components. The single reaction mixture is then contacted with an optional lytic reagent that differentially lyses non-nucleated red blood cells present in the sample and conserves the leukocyte populations and other nucleated populations in the sample. The resulting mixture is passed through a sensing region in a cell analyzer that measures the mixture for at least two parameters. In one embodiment, the passing step a single step that measures the mixture for at least two of the same or different parameters.

In one embodiment, this sensing region is a single flow aperture in a flow hematology analyzer. The parameters are selected from one or more channels of fluorescence, one or more optical parameters, and one or more electrical parameters, and combinations thereof. In one embodiment, one of the parameters is fluorescence. Populations of hematological cells in the sample are identified by analyzing at least two parameters for each cell population.

1. Method Employing Compositions with no Fluorescent Dye

In one embodiment of a method described herein, a single reaction mixture is formed by reacting the biological sample, e.g., about 10-200 μL, with the above described compositions comprising a "first" antibody, e.g., about 0.1 to about 2 μg. In one embodiment, about 100 μL of sample is used. The binding of this first antibody to an antigenic determinant on blood cells, e.g., a determinant that distinguishes between populations of leukocytes and non-leukocytes, in the sample is distinguishable from its binding to red blood cells and nucleated red blood cells. Optionally, an above-described "additional" antibody, e.g., about 0.1 to about 2 μg, labeled with either the same fluorochrome on the first antibody or with a second fluorochrome having a non-overlapping peak emission spectrum from that of the first fluorochrome, is introduced into the mixture. In desired embodiments employing two antibodies, the additional antibody permits the identification of different mature and immature granulocytes or myeloid cells. It allows the various types of immature cells to be distinguished from the "normal" or mature white cells. Although in one embodiment, the reaction mixture contains two antibodies, fewer or greater antibodies (i.e., 3) may be employed. For example, as described above, more than one additional antibody directed to an antigenic determinant that permits differentiation between other groups of normal and atypical cells (e.g., mature and immature granulocytes or myeloid cells), with appropriate labels may also be included in the reaction mixture. In certain embodiments, at least two of the fluorochromes have overlapping emission spectra which form a non-compensatable spectral pattern.

The components of the reaction mixture are allowed to react by incubating at room temperature. Generally ambient temperature is employed, although the temperature is not an issue. The incubation/reaction time range is from about 15 seconds to about 15 minutes. The reaction time for the reaction mixture of about 1 minute can be achieved if one adjusts the individual antibody and reagent concentrations, incorporating the use of sphering agents in the formulation and optimizing mixing. This type of rapid reaction time has been demonstrated in the laboratory and is required for an automated high throughput system.

In this embodiment of a method, a lytic system, with one or more reagents is introduced into the reaction mixture. Preferably, this step involves a lyse/quench reaction, which involves contacting a portion of the sample/antibody mixture with a lytic system or lytic reagent, as defined above, for about 4 to 10 seconds. The lytic system differentially lyses any non-nucleated red blood cells present in the sample while conserving the desired intrinsic and extrinsic properties of the leukocyte populations. After several seconds, the effect of the lytic system is then retarded or quenched with a quenching reagent as described and the RBCs are lysed, leaving in the sample, the leukocytes, the atypical cells, if any, and the nucleated RBCs. The quenching reagent generally is in contact with the sample, while the sample flows through the aperture in a cytometry/hematology analyzer. This second reagent is thus in contact with the mixture for at least a few seconds. Volumes of lytic reagent, quench reagent, and fixation reagent, if desired, can be readily selected by the person of skill in the art depending upon the identity of the lytic system used. The incubation of the reaction mixture and subsequent lytic and quenching cycles are preferably fully automated.

The sample containing the antibodies and any of the optional components, with or without lysed RBCs, is then passed through a sensing region, e.g., a single flow aperture in a transducer that is capable of making multiple correlated measurements (electrical, fluorescent and optical) on cells as they pass through a single aperture in the transducer module. The transducer thus provides a quantitative analysis of normal leukocytes and at least one (and preferably more than one) subpopulation of atypical leukocytes. As the cells pass through the transducer, multiple correlated electrical, fluorescent and optical measurements are made on each cell. The fluorescence of a cell is preferably measured within discrete, multiple wavelength ranges, which are determined by the respective fluorescence emission spectra of the dyes or fluorochromes used to label the antibodies which bind the cells. In one embodiment, the fluorescence analysis permits the identification of leukocytes from non-leukocytes in the sample, and permits the identification of at least one atypical cell subpopulation.

The optical parameter is generally one of light scatter, e.g., side scatter or forward light scatter. More than one angle of light scatter may be used where only a single fluorochrome is employed. The angle of light scatter may be selected from between about 10 to 70 degrees of light scatter, i.e. medium angle light scatter (MALS); between about 10 to 20 degrees of light scatters, i.e. lower medium angle light scatter (LMALS); between about 20 and about 70 degrees, i.e., upper medium angle light scatter (UMALS) or between about 80-100 degrees of light scatter, nominally orthogonal, i.e. side scatter (SS), low angle forward light scatter between about 2-18 degrees, and axial light loss or absorbance.

The electrical parameter is generally direct current electrical impedance measurement of volume (DC). Alternatively, the electrical parameter can be opacity, which is calculated as the radio frequency of the cell over the DC volume. These parameters are discussed and defined in detail in commonly assigned U.S. Pat. No. 5,125,737, which is incorporated herein by reference.

The above-described flow cytometric steps may be performed manually, partly manually and partly automated, or completely automated. One such automated flow cytometry instrument is described in U.S. Pat. No. 6,228,652, incorporated by reference herein, which discloses an automated instrument by which all of the aforementioned cell characteristics, i.e., DC volume, RF conductivity (opacity), light scatter and fluorescence characteristics, can be determined simultaneously, thereby obviating any need to correlate data gathered from separate transducers. The electrical measurements consist of DC (direct current volume/impedance) and RF (radio frequency). The optical measurements include light scattering and fluorescence. The light scatter measurements may consist of multiple angles of scatter collected on each cell to include low, medium and high forward angle measurements as well as right angle (90 degree/side scatter) measurements. The fluorescence measurements are made by collecting the fluorescence emission on two or three photomultiplier tubes or detectors (PMT).

Desirably useful in performing the analysis of the various embodiments described herein are hematology instruments that measure electrical, optical and fluorescence parameters. See e.g., the instrument described in U.S. Pat. No. 6,228,532, incorporated herein by reference. In an exemplary embodiment, a 532 nm green diode laser is used as the illumination source in a useful flow hematology system. However, for one skilled in the art, lasers with alternative emission lines, e.g., red laser such as 633 nm or 647 nm laser, blue lasers such as a 488 nm laser, can be substituted and the fluorochromes adjusted appropriately. Dyes may be tailored to the laser system.

The resulting data provides the information required to determine an extended leukocyte differential analysis. According to this method, each cell population is identified by at least two parameters, taking advantage of differing patterns of expression detectable in the fluorescence analysis of the fluorescence in the single reaction mixture. For example, the two parameters may be a channel of fluorescence and an optical parameter, such as side scatter. Another two parameters that may be used to identify a cell population may be two channels of fluorescence. Another two parameters that may be used to identify a cell population may be a channel of fluorescence and an electrical parameter, e.g., DC. Another two parameters that may be used to identify a cell population may be an optical parameter, e.g., SS, and an electrical parameter, e.g., DC. Additional combinations of the measurements made on the single reaction mixture are obvious to one of skill in the art, depending upon the particular fluorochromes, dyes, antibodies, optical and electrical parameters used in this method. These analytical steps are desirably incorporated into algorithms in an automated process.

For example, various cell populations can be identified by the following non-exclusive list of parameters identified in Table 3, depending upon the variation of the method used, the identity of the fluorochromes, antibodies, dyes, lasers, etc.

TABLE 3

| Cell Population Identified | Parameters Used for Analysis |
| --- | --- |
| Lymphocytes | DC + RLS; Florescence (FL) + SS |
| Monocytes | DC + RLS; SS + FL |
| Granulocytes | DC + RLS; FL + RLS; FL + SS; FL + FL |
| Eosinophils | FL + SS; DC + RLS; FL + FL |
| Basophils | DC + RLS + RF; FL + SS |
| Blasts | FS + FL; SS + FL; DC + FL |
| Immature Granulocytes | SS + FL; DC + FL; FL + FL |
| NRBC | 2 angles FS; FS + FL; FL + FL |
| NK cells | FL + SS; FL + DC; FL + FL |
| Atypical lymphocytes | FL + FL; SS + FL |
| B Cells | DC + FL; SS + FL; FL + FL |
| Non B Cells | SS + FL; DC + FL |
| Blast Cell lineage | FL + DC; FL + SS |
| Platelets | FS + SS; FS + FL |
| Immature Platelets | FS + FL |
| Reticulated RBCs | DC + FL; FS + FL |
| Bands | FL + SS |

In the embodiment of the method described above, this manipulation of the single reaction mixture permits the enumeration of greater than five up to seven or more hematologic cell populations in the sample.

Therefore, in an embodiment in which the first antibody, e.g., anti-CD45 and at least one additional antibody, e.g., anti-CD16, are labeled with the same fluorochrome (i.e., having identical peak emission spectra that overlap to form a non-separable spectral pattern), in the reaction mixture, after lysis, the various cell populations that can be identified using the parameters of fluorescence and an optical parameter or electrical parameter, and a new footprint pattern in the resulting histogram, include lymphocytes, monocytes, granulocytes, eosinophils, basophils, blasts, immature granulocytes, and NRBC.

Still other uses of the methods of certain embodiments demonstrate detection of nucleated red blood cells (NRBCs) in a peripheral blood specimen using the correlated multiparametric analysis of the methods described herein. NRBCs appear intermingled with debris in RLS and Opacity views. Since CD45 is expressed on cells of leukocyte lineage but not erythroid cells, the NRBCs are located within the CD45 negative population. Therefore NRBCs are first segregated from other nucleated cell populations by isolating the CD45 negative events. NRBCs appear as a CD45 negative, low SS population that overlaps debris but excludes other events such as aged or fragile leukocytes with poor CD45 expression. The NRBCs can then be separated from the debris by gating on the CD45 negative low SS events and displaying them in various angles of light scatter or electrical parameter in either single parameter or multiparameter views.

As another example is an embodiment in which the first antibody, e.g., anti-CD45 and at least one additional antibody, e.g., anti-CD16, are labeled with different fluorochromes. In certain embodiments, the two fluorochromes have overlapping peak emission spectra which form a non-compensatable spectral pattern. In the reaction mixture, after lysis, the various cell populations that can be identified using the parameters of fluorescence and an optical parameter or electrical parameter to provide a histogram with a new footprint, include the cells listed above including NK cells.

As another example, the first antibody, e.g., anti-CD45 and an additional antibody, e.g., anti-CD16, are labeled with the same fluorochrome (i.e., resulting in a non-compensatable spectral pattern), and another additional antibody, e.g., anti- CD19 is labeled with a different fluorochrome having a distinguishable emission spectra. In the reaction mixture, after lysis, the various cell populations that can be identified in a method described herein using the parameters of fluorescence and an optical parameter or electrical parameter, including a histogram showing a new footprint, include cells identified above as well as B cells, non-B cells and blast cell lineage.

Embodiments of methods described herein can differentially identify the five mature leukocyte populations normally found in peripheral blood (lymphocytes, monocytes, granulocytes, eosinophils & basophils), as well as identify hematopoietic cells that lack the expression of CD45, such as cells of the erythroid and megakaryocytic lineages; and identify the most undifferentiated cells, such as stem cells and blasts.

In an embodiment wherein three monoclonal antibodies and two fluorochromes, e.g., anti-CD16 fluorescence in conjunction with anti-CD19 and anti-CD45, conjugated to a different fluorochrome, are employed with the additional "sizing" parameter, the method identifies B cells, NK cells, and non-B/non-NK (T) cells; identifies and subcategorizes blasts into at least two groups (B lymphoblasts and non-B lymphoblasts), categorizes benign lymphoproliferative processes into B, NK and non-B/NK processes; identifies and distinguishes between B cell chronic and B cell acute lymphoproliferative processes; and identifies subsets of atypical lymphocytes that represent acute or chronic B cell neoplasms.

A particular example of this embodiment is described below in Example 10. The single reaction mixture included optimal concentrations of anti-CD45-PC5 (Phycoerythrin-Cyanine 5) as the first antibody, and used additional antibodies, anti-CD19-PE (Phycoerythrin), anti-CD16-PE. A variety of substitutions or additions to the monoclonal cocktail are possible to produce the same or similar sets of data as described in Example 10.

2. Method Involving a Single Reaction Mixture With a Fluorescent Dye

In another embodiment, a single reaction mixture is formed by reacting the biological sample with a fluorescent dye having a characteristic dye emission spectrum and an above-described "first" antibody labeled with a fluorochrome having a first peak emission spectrum. Various additional embodiments may employ an above-described "additional" antibody, labeled with either the same fluorochrome as on the first antibody or with a second fluorochrome having a second peak emission spectra from that of the first fluorochrome, in the same manner as described in the first method described above. As described above in the various compositions, at least two of the first peak emission spectrum, the dye emission spectrum and the optional second peak emission spectrum overlap to form a non-compensatable spectral pattern.

In one embodiment of this method, the fluorescent dye is introduced into the reaction mixture at a concentration of about 10 µL of a 0.5 µg/mL to about 20 µg/mL solution. Lower or higher concentrations are possible if one adjusts the antibody concentrations, blood volumes, incubation and/or mixing times, appropriately. This fluorescent dye has a dye emission spectrum that may or may not overlap with the peak emission spectrum of at least one fluorochrome-labeled antibody in the single reaction mixture. Preferably, the peak emission spectra of at least one fluorochrome i S label(s) on at least one antibody in the mixture overlaps the dye emission spectra to form a new spectral pattern that is non-compensatable. The resulting fluorescence signals detected in any channel of the detection system are characteristic of either the fluorescence emission of the dye alone, the fluorochrome conjugated antibody(s) alone, or the non-compensatable product of the additive fluorescence of the dye and at least one fluorochrome conjugated antibody(s).

These components of the reaction mixture are permitted to react under the same conditions as described above for the first method embodiment. In this present embodiment, the lytic system may be omitted from the reaction mixture, or it may be added to the reaction mixture as described for the embodiment above. Omission of the lytic system from this method permits the enumeration of non-nucleated cell parameters, such as reticulated RBCs or reticulated RBC hemoglobin or megakaryocytes or platelets, if desired.

The resulting single reaction mixture containing the sample, the antibodies, the fluorescent dye, with or without lysed RBCs is then passed through a sensing region of a cell analyzer. Preferably, such a sensing region is a single flow aperture in a transducer that is capable of making multiple correlated measurements (electrical and optical) simultaneously on cells as they pass through a single aperture in the transducer module. The operation of the flow cytometer is as described above, and analysis is then made of the cell populations in the sample based upon use of two of the parameters (fluorescence, optical and electrical) per population, also as described above. A new footprint is detectable in a histogram as described heretofore.

In one embodiment the parameters used for this evaluation include forward and side scattered light and a minimum of at least two channels of fluorescence. The fluorescence emission pattern in each of the collected channels is representative of either the dye alone, the fluorochrome conjugated monoclonal antibody alone, or the spectral addition of the dye and at least one of the fluorochrome conjugated monoclonal antibodies in the reaction mixture. However, the method might also employ the VCS parameters of impedance (DC) and conductivity (RF) along with light scatter and fluorescence measurements. As indicated above, a number of suitable lasers may be employed to excite the fluorescence, including a 488nm blue argon laser, a green 532 nm laser, or a red laser (633 nm, 635 nm, 640 nm or 644 nm) if the dye is a red excitable dye used in combination with antibodies conjugated to red excitable fluorochromes.

In the embodiment of the method described above, this manipulation of the single reaction mixture permits the enumeration of at least six to seven or more hematologic cell populations in the sample. The collected multiparametric data is then analyzed and two parameters per cell population are employed to identify each cell population. For example, at least one size parameter (FS, SS, or DC) in combination with at least one channel of fluorescence data or alternatively two channels of fluorescence data are used to produce an extended differential analysis. The cell populations that are identified by this method include at least the following populations: lymphocytes, monocytes, neutrophils, eosinophils, basophils, NRBCs, blasts, immature granulocytes, atypical/variant lymphocytes. Additional cell populations that are identifiable using embodiments of the methods described herein include hematopoietic stem cells, hematagones, blast lineage, myeloid maturity index, RBC maturity index, myeloid to erythroid ratio and fragile white cell fractions, NK cells, bands, etc.

With regard to the specific embodiments described herein and in the examples below, substitutions or additions to the monoclonal antibodies contained in the mixture can be made without affecting the ability to produce the same or similar sets of data. The fluorochromes conjugated to specific antibodies can also be changed so that any of the fluorochromes in Table 1 or 2 are utilized, or the non-compensatable fluorochromes identified above, that overlap other portions of the fluorescent dye emission spectrum are used. The dyes also exemplified in those tables are also used in these embodiments. In certain embodiments, one or more pairs of non-compensatable dyes and fluorochromes in Tables 1 and 2 are employed in this method. Additionally, the antibodies can have different conjugates so that individual antibodies overlap different portions of the dye emission spectrum. The RBC lytic reagent can also vary with the primary requirement being the conservation of the antigenic determinants on the cells of interest and the conservation of the desired intrinsic properties of the cells of interest. These alterations to the described reagent system can be employed by one who is skilled in the art without compromising the ability to obtain substantially the same results.

As one embodiment described herein and illustrated in Example 15, one antibody is employed, anti-CD16, labeled with PE. The nucleic acid dye Acridine Orange has a dye emission spectrum that overlaps with the peak emission spectrum of PE to form a non-compensatable spectral pattern. A lytic system is also employed. Following the method, 7 cell populations are identified using the single antibody and overlapping nucleic acid dye. Similarly, Example 16 demonstrates the use of a single antibody, e.g., anti-CD45-PE, with a peak emission spectrum overlapping the dye emission spectrum, and a lytic system, with similar results. FIGS. 11A and 11B identify the enumerated cell populations.

As an example, the first antibody, e.g., anti-CD45 and at least one additional antibody, e.g., anti-CD16, are labeled with the same fluorochrome (i.e., overlapping peak emission spectra that form a non-separable spectral pattern), and the fluorescent dye Acridine Orange is added to the reaction mixture, without lysis. The various cell populations that can be identified using the parameters of fluorescence and an optical parameter or electrical parameter, include those identified previously, and further including platelets, reticulated platelets, and reticulated RBCs.

Another example provides the first antibody, e.g., anti-CD45 and at least one additional antibody, e.g., anti-CD16, labeled with the same fluorochrome. The nucleic acid dye Acridine Orange is added to the reaction mixture with the lytic system. The various cell populations that can be identified using the parameters of fluorescence and an optical parameter or electrical parameter, include lymphocytes, monocytes, granulocytes, eosinophils, basophils, immature granulocytes, blasts, NRBCs, NK cell and atypical or variant lymphocytes.

Another example provides the first antibody, e.g., anti-CD45 and at least one additional antibody, e.g., anti-CD16, labeled with different fluorochromes. The nucleic acid dye Acridine Orange is added to the reaction mixture, with the lytic system. The various cell populations that can be identified using the parameters of fluorescence and an optical parameter or electrical parameter, include lymphocytes, monocytes, granulocytes, eosinophils, basophils, immature granulocytes, blasts, NRBCs, NK cell, atypical or variant lymphocytes, activated monocytes, and bands.

The examples below further illustrate other embodiments of this variation of the method and illustrate the identification of multiple cell populations in the samples.

As one of skill in the art can readily determine from the teachings herein, many other variations of these methods can be exemplified by using different fluorescence, optical and electrical parameter pairs and selected antibodies, fluorochromes and dyes, as well as other optional components for the reaction mixtures. These variations are readily apparent from the above descriptions. All variations to the described method are expected to be obvious to the person of skill in the art, based on the disclosure herein and the information known in the art.

A minimalist approach is thereby demonstrated in the number of transducers, hardware, fluorochromes and monoclonal reagents used to perform an extended cell differential in a single analytical process. The methods described herein offer many advantages or improvements over current methods of hematological analysis. Among these advantages are a more robust, extended differential that can include from 7, 8, 9, 10 to about 11 cell populations identified in a single reaction mixture. These methods offer more and alternative means for determining the basic differential, i.e., to apply an algorithm to the cell populations, e.g., lymphocytes, monocytes, neutrophils, eosinophils and basophils such as in the illustrated figures referenced herein. This opportunity is particularly important when the significant cells in the biological specimen are in the presence of conditions that may interfere with one particular approach to population determinations. For example, such interfering conditions occur with certain types of chemical interference, age, cell fragility, and/or the presence of atypical cell types that obscure the evaluation of a normal 5-part differential.

The ability to positively identify cells by multiparametric electrical and optical measurements in a single analysis vastly improves the ability to positively identify and select for additional clinically relevant blood cell populations, such as atypical cell types. Such selection eliminates the high false positive or false negative determinations that plague current methods of hematological analysis.

The methods described herein further extend the ability to provide new information that cannot be obtained by the parametric limitations on current hematology analyzers. The automation of these analyses substantially improves the efficiency of the hematology laboratory by eliminating unnecessary labor and more efficiently directing the workflow for further testing and analysis.

EXAMPLES

The following examples illustrate various aspects of the invention. These examples do not limit the scope of this invention that is defined by the appended claims.

The following Examples 1-9 employ two antibodies: anti-CD45 and anti-CD16. Examples 10-13 employ one antibody, either anti-CD45 or anti-CD16. The CD45 antigen is expressed by most cells in the leukocyte lineage but not expressed on other hematopoietic cells such as erythrocytes and megakaryocytes. It is also known to display differential expression within the leukocytes so that lymphocytes exhibit relatively high expression, whereas basophils have lower expression. Expression of the CD45 antigen can also vary as a function of leukocyte maturation level with blasts or stem cells expressing less CD45 antigen than their mature counterparts. Therefore, the combination of AO fluorescence and anti-CD45 fluorescence, in conjunction with light scatter and/or an electrical measurement, such as DC, can be used to (1) differentially identify the leukocyte populations normally found in peripheral blood (lymphocytes, monocytes, granulocytes, eosinophils & basophils) (2) identify hematopoietic cells that lack the expression of CD45 such as cells of the erythroid and megakaryocytic lineages (3) and identify the most undifferentiated cells, such as stem cells and blasts.

In contrast, the distribution of the CD16 antigen is more restricted with regard to leukocyte expression. The CD16 antigen has two isoforms, CD16 alpha and CD16 beta. CD16 beta is expressed strongly on segmented neutrophils and bands and poorly or not at all on other leukocytes. CD16 alpha follows a similar pattern of expression except that it is also expressed on a subset of leukocytes classified as natural killer cells and activated monocytes. This method allows for enhanced separation between neutrophils and eosinophils in a sample that has CD16 added compared to the spatial separation observed in the absence of CD16. This enhanced separation is obtained because mature segmented neutrophils express the CD16 antigen but eosinophils have either less or no CD16 antigen present. Therefore CD16 can be used to enhance the separation in these two populations. The CD16 antigen is also more weakly expressed or absent on immature granulocytes (metamyelocytes, myelocytes and promyelocytes) than on neutrophils.

Therefore, the separation and identification of various nucleated cell populations can be achieved by the use of anti-CD16 in the methods described herein. The presence of these populations may differ in the views of the different fluorescence channels. Various embodiments of the methods and compositions described herein thus provide the ability to have multiple analytical strategies or algorithms for identification and enumeration of the desired cell types.

Therefore, in conjunction with AO fluorescence, anti-CD45 fluorescence, light scatter and/or electrical measurements, anti-CD16 fluorescence can identify and distinguish between differentiated myeloid cells, immature myeloid precursors and stem cells or blasts. Because the CD16 antigen may be more conserved than the intrinsic properties of neutrophils, it can also be used to identify degranulated(ing) neutrophils such as may occur due to age, therapeutic treatments and certain hypogranular conditions. In addition, natural killer cells and activated monocytes can be identified.

Example 1

A single reaction mixture was prepared by reacting 100 μL of normal human peripheral blood with about 1 μg of anti-CD45-PC7, i.e., a first antibody labeled with a first fluorochrome having a first emission spectrum, the first antibody binding to an antigenic determinant that is differentially expressed on populations of leukocytes and non-leukocytes and about 1 μg of anti-CD16-PC7, i.e., an additional antibody labeled with same fluorochrome having the same emission spectrum. The anti-CD16 antibody binds to an antigenic determinant that is differentially expressed on populations of mature and immature granulocytes or myeloid cells. This reaction mixture is mixed briefly and incubated at room temperature for approximately 10 minutes. The reaction was performed in the absence of a fluorescent dye.

This reaction mixture is then reacted for about 8 seconds with the lytic system (about 600 μL of Immunoprep™ reagent A; see U.S. Pat. No. 5,030,554) that differentially lyses the non-nucleated red blood cells in the blood specimen while conserving the desired intrinsic and extrinsic properties of the nucleated cell populations including leukocytes and nucleated red blood cells. After about 8 seconds, the quenching reagent (Immunoprep™ reagent B; 265 μL) is introduced into the mixture for 10 seconds, to terminate the lytic reaction. No fixation was used.

Thereafter, the mixture is allowed to flow into a transducer module that is capable of making multiple correlated measurements (fluorescent and optical) on cells as they pass through a single aperture in the transducer module. This flow cytometry system is capable of measuring 5 channels of fluorescence in combination with side scatter (90 degrees) and forward scatter (2-18 degrees). The system utilizes a blue argon ion laser as an excitation source for the fluorescence detection, although the method can also employ a green laser excitation source and obtain equal or better results.

The results of this exemplary hematological analytic process are displayed in dual parameter histograms of FIG. 1A (displaying results of FS+SS, permitting identification of 3 cell populations), FIG. 1B (displaying FL of PC7 vs. SS, permitting identification of 5 cell populations), and FIG. 1C (displaying FL of PC7 vs. FS, permitting identification of 3 cell populations), as described above in figure descriptions. The analysis is performed offline on listmode data files of each acquisition using commercially available software such as RXP or CXP software (Beckman Coulter, Inc.) or Winlist™ software (Verity Software), or freeware such as WinMD1 software.

More two parameter combinations than are shown can be used in the determination of cell populations. The figures are simplified for ease of presentation as two-dimensional scattergrams. The figures demonstrate that the monoclonal cocktail in conjunction with other optical parameters provide a much more hardy and robust differential. Multiple views are provided by this method in which basophils can be identified. With regard to extended differential cell types, the area where blasts would be expected to appear may be observed in a log CD45 vs. SS view. In this dimension, as well as in alternative light scatter dimensions, blasts would not obscure the presence of normal cell types and therefore both the 5-part differential and blast detection/enumeration can be performed. Blasts are sometimes described as atypical lymphocytes upon manual examination. The categorization of cells as atypical lymphocytes is quite broad (blasts, CLLs, reactive and or activated lymphocytes) and this description is usually a signal to initiate further clinical testing. The characterization of blasts demonstrates distinct patterns that differentiate them from other types of cells in the peripheral blood. These include, but are not restricted to, low to no expression of the CD45 antigen, increased light scatter and increased electrical impedance (DC) as compared to normal small lymphocytes. Therefore, blasts that are described morphologically as atypical lymphocytes or any other description can be identified as blasts by the present method. Chronic lymphocytic leukemias are often but not always described morphologically as atypical lymphocytes.

Since immature granulocytes express CD16 poorly or not at all, mature and immature granulocytes can be differentiated from each other as well as other cell types including NK cells and activated monocytes.

Example 2

A single reaction mixture was prepared by reacting 100 μL of normal human peripheral blood with about 1 μg of anti-CD45-PE, i.e., a first antibody labeled with a first fluorochrome having a first emission spectrum, the first antibody binding to an antigenic determinant that is differentially expressed on populations of leukocytes and non-leukocytes and about 1 μg of anti-CD16-PC7, i.e., an additional antibody labeled with a second fluorochrome that has an emission spectrum distinguishable from the emission spectrum of the fluorochrome PE. The anti-CD16 antibody binds to an antigenic determinant that is differentially expressed on populations of mature and immature granulocytes or myeloid cells. This reaction mixture is mixed briefly and incubated at room temperature for approximately 10 minutes. The reaction was performed in the absence of a fluorescent dye.

This reaction mixture is then reacted for about 8 seconds with the lytic system (about 600 μL of Immunoprep™ reagent A; see U.S. Pat. No. 5,030,554) that differentially lyses the non-nucleated red blood cells in the blood specimen while conserving the desired intrinsic and extrinsic properties of the nucleated cell populations including leukocytes and nucleated red blood cells. After about 8 seconds, the quenching reagent (Immunoprep™ reagent B; 265 µL) is introduced into the mixture for 10 seconds, to terminate the lytic reaction. No fixation was used.

Thereafter, the mixture is allowed to flow into a transducer module that is capable of making multiple correlated measurements (fluorescent and optical) on cells as they pass through a single aperture in the transducer module.

Figure 2B:
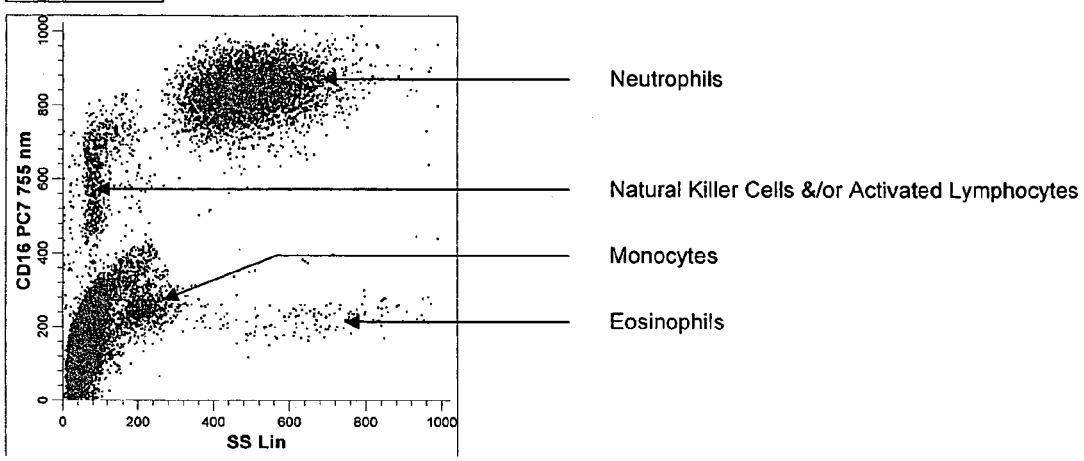
Figure 2C:
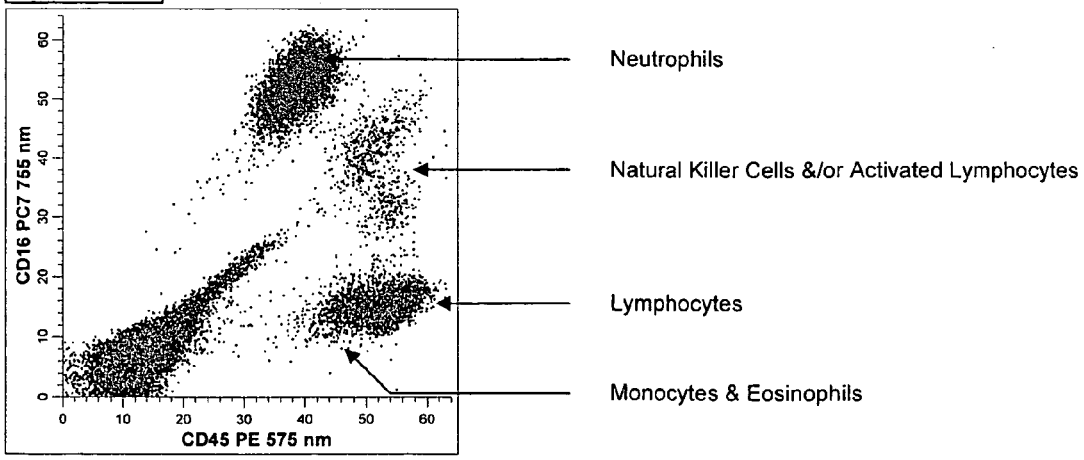

The results of this exemplary hematological analytic process are displayed in the dual parameter histograms of FIGS. 2A thru 2C. FIG. 2A is a two parameter histogram displaying CD45-PE fluorescence vs. side scatter (SS). At least four cellular populations are identified and enumerated in this display: lymphocytes, monocytes, basophils and a cluster of granulocytes containing eosinophils and neutrophils. FIG. 2B is a two parameter histogram displaying fluorescence of CD16-PC7 vs. side scatter (SS). At least four cellular populations are identified and enumerated in this display: neutrophils, monocytes, eosinophils and a cluster containing natural killer cells and/or activated lymphocytes. FIG. 2C is a two parameter histogram displaying CD16-PC7 fluorescence vs. CD45-PE fluorescence. At least four cellular populations are identified and enumerated in this display: lymphocytes, neutrophils, a cluster containing eosinophils and monocytes and an additional bimodal cluster containing natural killer cells and/or activated lymphocytes.

Example 3

A single reaction mixture was prepared by reacting 200 µL of normal human peripheral blood with about 1 µg of anti-CD45-PC5, i.e., a first antibody labeled with a first fluorochrome having a first emission spectrum, the first antibody binding to an antigenic determinant that is differentially expressed on populations of leukocytes and non-leukocytes and about 1 µg of anti-CD16-PE, i.e., an additional antibody labeled with a second fluorochrome that has an emission spectrum distinguishable from the emission spectrum of the fluorochrome PC5. The anti-CD16 antibodybinds to an antigenic determinant that is differentially expressed on populations of mature and immature granulocytes or myeloid cells. This reaction mixture is mixed briefly and incubated at room temperature for approximately 10 minutes. The reaction was performed in the absence of a fluorescent dye.

A portion (about 34 µL) of this reaction mixture is then reacted for about 6 seconds with the lytic system (about 556 µL of the Synlyse system; see U.S. Pat. No. 6,573,102 and 5,763,280) that differentially lyses the non-nucleated red blood cells in the blood specimen while conserving the desired intrinsic and extrinsic properties of the nucleated cell populations including leukocytes and nucleated red blood cells After about 6 seconds, the quenching reagent (Stabilyse; 240 µL) is introduced into the mixture for 10 seconds, to retard the lytic reaction. No fixation was used.

Thereafter, the mixture is allowed to flow into a transducer module that is capable of making multiple correlated measurements (electrical, fluorescent and optical) on cells as they pass through a single aperture in the transducer module (see U.S. Pat. No. 6,228,652).

FIGS. 3A thru 3C are dual parameter histograms displaying the results of this experiment. FIG. 3A displays DC (Impedance) vs. Median Angle Light Scatter (MALS) which is a forward angle of light scatter from approximately 20 to 40 degrees. At least four cellular populations are identified and enumerated in this display: lymphocytes, monocytes, neutrophils and eosinophils. FIG. 3B displays CD45-PC5 fluorescence vs. Opacity (OP) where OP=Radio Frequency (RF)/Impedance (DC) following removal of the neutrophils and eosinophils by gating them out from histogram FIG. 3A. Three cellular populations are identified and enumerated: activated lymphocytes, activated monocytes and basophils. FIG. 3C displays CD16-PE fluorescence vs. RF. Three cellular populations are identified and enumerated in this display: lymphocytes, monocytes and neutrophils.

Example 4

A single reaction mixture was prepared by reacting 200 µL of a human peripheral blood specimen containing immature granulocytes and bands, with about 1 µg of anti-CD45-PC5, i.e., a first antibody labeled with a first fluorochrome having a first emission spectrum, the first antibody binding to an antigenic determinant that is differentially expressed on populations of leukocytes and non-leukocytes and about 1 µg of anti-CD16-PE, i.e., an additional antibody labeled with a second fluorochrome that has an emission spectrum distinguishable from the emission spectrum of the fluorochrome PC5. The anti-CD16 antibody binds to an antigenic determinant that is differentially expressed on populations of mature and immature granulocytes or myeloid cells. This reaction mixture is mixed briefly and incubated at room temperature for approximately 10 minutes. The reaction was performed in the absence of a fluorescent dye.

A portion (about 34 µL) of this reaction mixture is then reacted for about 6 seconds with the lytic system (about 556 µL of the Synlyse system; see U.S. Pat. No. 6,573,102 and 5,763,280) that differentially lyses the non-nucleated red blood cells in the blood specimen while conserving the desired intrinsic and extrinsic properties of the nucleated cell populations including leukocytes and nucleated red blood cells. After about 6 seconds, the quenching reagent (Stabilyse; 240 µL) is introduced into the mixture for 10 seconds, to retard the lytic reaction. No fixation was used.

Thereafter, the mixture is allowed to flow into a transducer module that is capable of making multiple correlated measurements (electrical, fluorescent and optical) on cells as they pass through a single aperture in the transducer module (see U.S. Pat. No. 6, 228,652).

FIGS. 4A thru 4D are dual parameter histograms providing an analysis of this sample based on the methods described herein. FIG. 4A displays DC (Impedance) vs. Median Angle Light Scatter (MALS). At least four cellular populations are identified and enumerated in this display: lymphocytes, monocytes, eosinophils and a cluster containing neutrophils, bands and immature granulocytes. FIG. 4B displays fluorescence of CD16-PE vs. SS. At least three cellular populations are identified and enumerated: neutrophils, bands and a cluster containing natural killer cells and/or activated lymphocytes. FIG. 4C displays DC vs. MALS following removal of the neutrophils and bands by gating them out from the histogram in FIG. 4B. At least four cellular populations are identified and enumerated in this display: lymphocytes, monocytes, eosinophils and immature granulocytes. FIG. 4D displays fluorescence of CD45-PC5 vs. SS following removal of the neutrophils and bands by gating them out from the histogram in FIG. 4B. At least five cellular populations are identified and enumerated in this display: lymphocytes, monocytes, eosinophils, basophils and immature granulocytes.

Example 5

A single reaction mixture was prepared by reacting 100 μL of normal human peripheral blood with about 1 μg of anti-CD45-PC7, the first antibody, and about 1 μg of anti-CD16-PC7, the additional antibody labeled with the same fluorochrome. The antibody concentrations (about 1 μg each) are optimized based on titration of the individual antibodies. Optimal concentrations were defined based upon desired staining intensity and reaction kinetics. This reaction mixture is mixed briefly and incubated at room temperature for approximately 10 minutes. The reaction mixture was then contacted with a fluorescent dye (Acridine Orange; approximately 1.25 μg/mL), which has an emission spectrum that overlaps with the emission spectra of PC7. The dye PC7 has a peak emission wavelength of approximately 770 nm when excited with a blue or green laser. In contrast, the Acridine Orange emission spectrum extends from the low 500 nm range to greater than 755 nm when staining subcellular elements in situ (when excited with a blue laser). This is in contrast to the emission of Acridine Orange in solution where the spectral emission is minimal to non-existent at 700 nm. The overlap between the AO and PC7 is compensatable. The overlapping peak emission spectra of the two PC7 fluorochromes labeling the two different antibodies form a non-compensatable spectral emission pattern.

This mixture was analyzed according to a method described herein, but without lysing the red blood cells present in the sample. The mixture was allowed to flow into a transducer module that is capable of making multiple correlated measurements (fluorescent and optical) on cells as they pass through a single aperture in the transducer module.

FIGS. 5A thru 5C are dual parameter histograms demonstrating the results. The RBCs are not apparent in the histograms since they were purposely set below the electronic threshold of the system in order to emphasize the quantity of white blood cell events collected. FIG. 5A displays AO fluorescence at a wavelength of approximately 675 nm vs. SS. At least four cellular populations are identified and enumerated in this display: lymphocytes, monocytes, eosinophils and neutrophils. FIG. 5B displays the fluorescence of AO, CD16-PC7 & CD45-PC7 at a wavelength of approximately 755 nm vs. SS. At least six cellular populations are identified and enumerated: lymphocytes, monocytes, neutrophils, eosinophils, basophils and a cluster containing natural killer cells and/or activated lymphocytes. FIG. 5C displays the fluorescence of AO, CD16-PC7 & CD45-PC7 at a wavelength of approximately 755 nm vs. the fluorescence of AO at a wavelength of approximately 675 nm. At least six cellular populations are identified and enumerated: lymphocytes, monocytes, neutrophils, eosinophils, basophils and a cluster containing natural killer cells/and or activated lymphocytes.

Example 6

A single reaction mixture was prepared by reacting 100 μL of normal human peripheral blood with about 1 μg of anti-CD45-PC7 (the first antibody), and about 1 μg of anti-CD16-PE (the additional antibody labeled with a fluorochrome having a different emission spectrum from that of PC7). The reaction mixture was then contacted with Acridine Orange (approximately 1.25 μg/mL), which has an emission spectrum that overlaps with the peak emission spectra of PE to form a non-compensatable spectral pattern. This reaction mixture is mixed briefly and incubated at room temperature for approximately 10 minutes.

The sample was then passed through a single flow aperture in a flow hematology analyzer without lysing the red blood cells present in the sample. The RBCs are not apparent in the histogram displays as they were set below the electronic threshold of the system in order to maximize the quantity of white blood cell events displayed.

FIGS. 6A and 6B are dual parameter histograms displaying the results of this experiment. FIG. 6A displays AO and CD16-PE fluorescence at a wavelength of approximately 575 nm vs. SS. At least five cellular populations are identified and enumerated in this display: lymphocytes, monocytes, eosinophils, neutrophils and a cluster containing natural killer cells and/or activated lymphocytes. FIG. 6B displays AO & CD45-PC7 fluorescence at a wavelength of approximately 755 mn vs. SS. At least four cellular populations are identified and enumerated: lymphocytes, monocytes, neutrophils, and basophils.

Example 7

A single reaction mixture was prepared by reacting 100 μL of an abnormal human peripheral blood specimen with about 1 μg of anti-CD45-PC7, the first antibody, and about 1 μg of anti-CD16-PC7, the additional antibody labeled with the same fluorochrome. Therefore the two antibodies have overlapping peak emission spectra. The reaction mixture was then contacted with approximately 1.25 μg/mL of the fluorescent dye (Acridine Orange), which has an emission spectrum that does not overlap (or only overlaps in a compensatable or distinguishable manner) with the emission spectra of PC7. This reaction mixture is mixed briefly and incubated at room temperature for approximately 10 minutes.

This reaction mixture is then reacted for about 8 seconds with the lytic system (about 600 μL of Immunoprep™ reagent A; see U.S. Pat. No. 5,030,554) that differentially lyses the non-nucleated red blood cells in the blood specimen while conserving the desired intrinsic and extrinsic properties of the nucleated cell populations including leukocytes and nucleated red blood cells. After about 8 seconds, the quenching reagent (Immunoprep™ reagent B; 265 μL) is introduced into the mixture for 10 seconds, to terminate the lytic reaction. No fixation was used.

Thereafter, the mixture is allowed to flow into a transducer module that is capable of making multiple correlated measurements (fluorescent and optical) on cells as they pass through a single aperture in the transducer module.

Figure 7A:
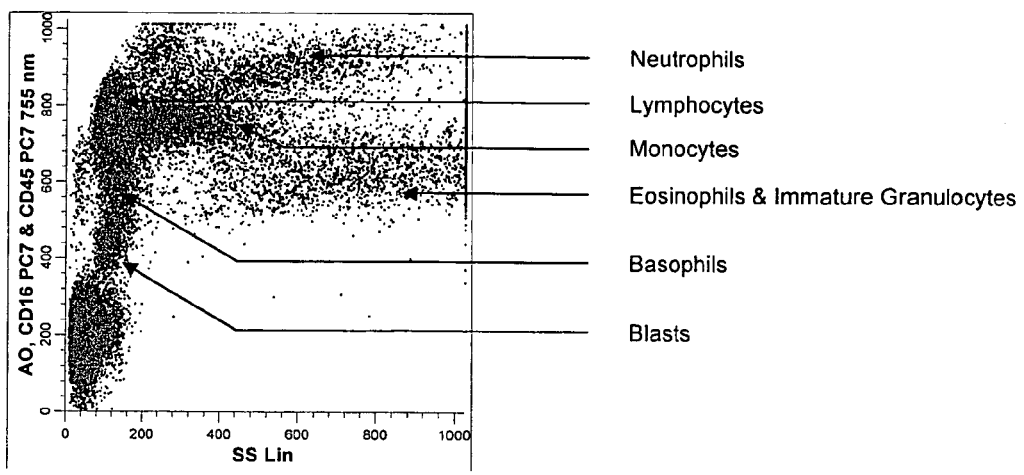
FIGS. 7A thru 7C are dual parameter histograms obtained by performing a method described herein in which an abnormal peripheral blood specimen was reacted with a first antibody labeled with a first fluorochrome (CD45 PC7) having a first peak emission spectrum, the first antibody binding to an antigenic determinant that is differentially expressed on populations of leukocytes and non-leukocytes. An additional antibody, labeled with the same first fluorochrome (CD16-PC7), binds to an antigenic determinant that is differentially expressed on populations of mature and immature granulocytes or myeloid cells. Thus the fluorochromes on the two antibodies overlap to form a non-compensatable, non-separable spectral emission. The fluorescent dye (Acridine Orange), which has a peak emission spectrum that does not overlap or overlaps with the peak emission spectrum of PC7 in a compensatable manner, is also part of this experiment. A lytic system is used to differentially lyse any non-nucleated red blood cells present in the sample and conserve the leukocyte population in the sample. When utilizing the compositions described herein consisting of fluorescent dyes and fluorochrome labeled antibodies with overlapping spectra that cannot be separated or distinguished based upon optical or electronic compensation means, a new fluorescent footprint is established. This new fluorescent footprint is a result of the overlapping spectra and the combined cellular staining patterns of the dyes and fluorochrome labeled antibodies chosen for the composition. The new fluorescent footprint results in histogram patterns that are useful for the identification of additional cell populations or subtypes in hematological disease.
Figure 7B:
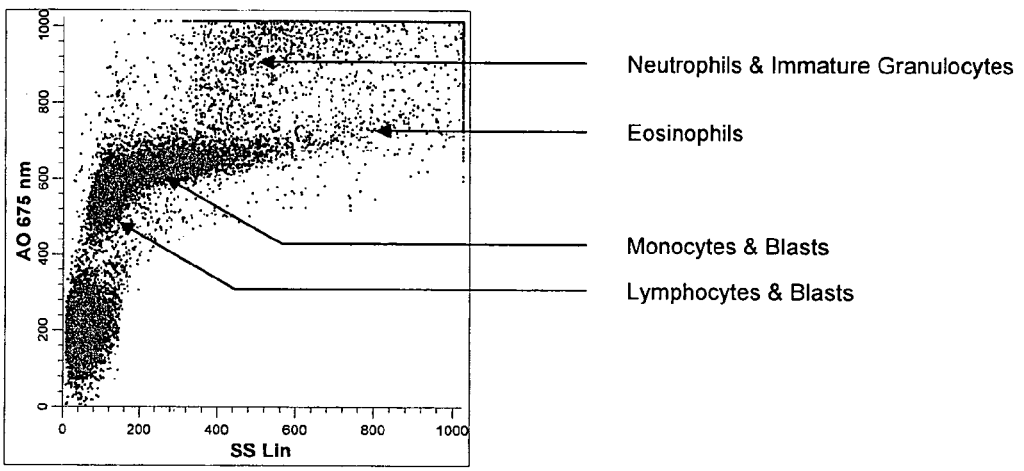
Figure 7C:
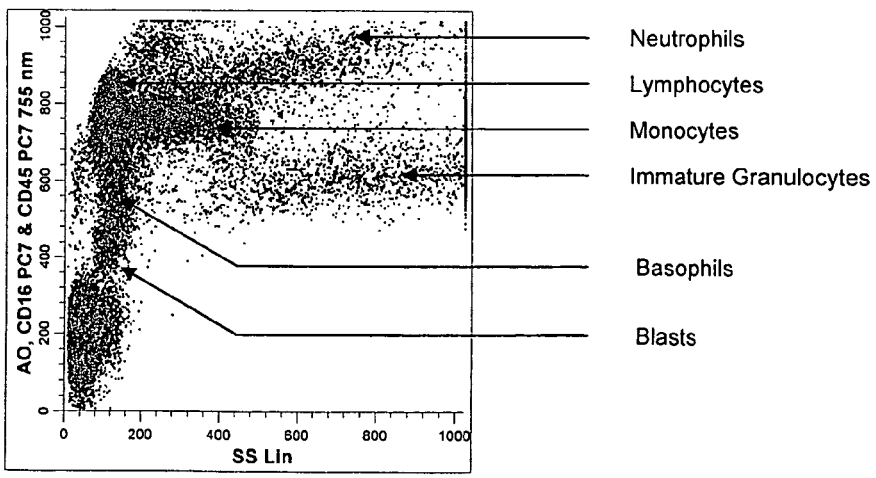

FIGS. 7A thru 7C are dual parameter histograms displaying the results of this analysis. FIG. 7A displays AO, CD16-PC7 & CD45-PC7 fluorescence at a wavelength of approximately 755 nm vs. SS. At least six cellular populations are identified and enumerated in this display: lymphocytes, monocytes, neutrophils, basophils, blasts and a cluster containing eosinophils and immature granulocytes. FIG. 7B displays AO fluorescence at a wavelength of approximately 675 nm vs. SS. At least four cellular populations are identified and enumerated: eosinophils, a cluster containing neutrophils and immature granulocytes, a cluster containing lymphocytes and blasts and an additional cluster containing monocytes and blasts. FIG. 7C displays AO, CD16-PC7 & CD45-PC7 fluorescence at a wavelength of approximately 755 nm vs. SS following removal of the eosinophils by gating them out from FIG. 7B. At least six cellular populations are identified and enumerated in this display: lymphocytes, monocytes, neutrophils, basophils, blasts and immature granulocytes.

Example 8

A single reaction mixture was prepared by reacting 100 µL of an abnormal human peripheral blood with about 1 µg of anti-CD45-PC7, the first antibody, and about 1 µg of anti-CD16-PE, the additional antibody labeled with a fluorochrome having a different peak emission spectrum from that of PC7. The reaction mixture was then contacted with approximately 1.25 µg/mL of Acridine Orange, which has an emission spectrum that overlaps with the peak emission spectra of PE to form a spectral pattern that is not compensatable or resolvable by optics or color compensation. This reaction mixture is mixed briefly and incubated at room temperature for approximately 10 minutes.

This reaction mixture is then reacted for about 8 seconds with the lytic system (about 600 µL of Immunoprep™ reagent A; see U.S. Pat. No. 5,030,554) that differentially lyses the non-nucleated red blood cells in the blood specimen while conserving the desired intrinsic and extrinsic properties of the nucleated cell populations including leukocytes and nucleated red blood cells. After about 8 seconds, the quenching reagent (Immunoprep™ reagent B; 265 µL) is introduced into the mixture for 10 seconds, to terminate the lytic reaction. No fixation was used.

Thereafter, the mixture is allowed to flow through a single flow aperture in a flow hematology analyzer that is capable of making multiple correlated measurements (fluorescent and optical) on cells as they pass through a single aperture in the transducer module.

Figure 8A:
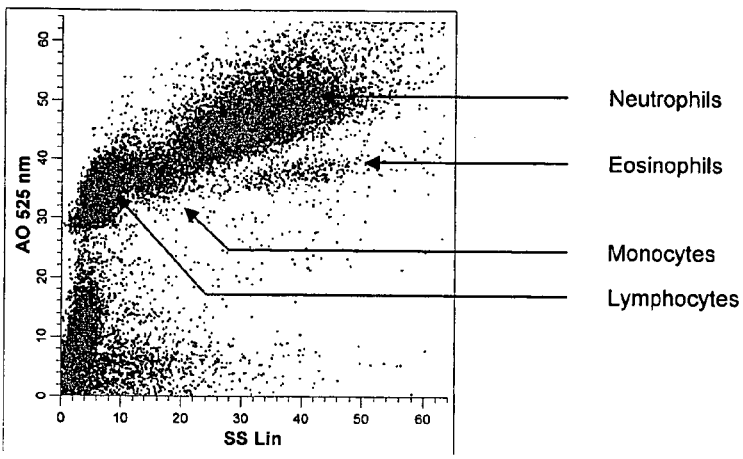
FIGS. 8A thru 8C are dual parameter histograms obtained by performing a method described herein in which an abnormal peripheral blood specimen was reacted with a first antibody labeled with a first fluorochrome (CD45-PC7) having a first peak emission spectrum. The first antibody binds to an antigenic determinant that is differentially expressed on populations of leukocytes and non-leukocytes. An additional antibody labeled with an additional fluorochrome (CD16-PE), binds to an antigenic determinant that is differentially expressed on populations of mature and immature granulocytes or myeloid cells. The additional fluorochrome has an additional peak emission spectrum distinguishable from the first peak emission spectrum. The fluorescent dye (Acridine Orange) which has a peak emission spectrum that overlaps with the peak spectrum of PE and a lytic system that differentially lyses any non-nucleated red blood cells present in the sample and conserves the leukocyte population in the sample are also used. As provided above, the overlap between AO and PE forms a new non-separable spectral emission that, upon fluorescent analysis, with the different cellular distribution patterns and specificities of the antibodies and fluorescent dyes used results in one or more histograms characterized by the presence of a new "footprint". The new footprint is a new fluorescent cellular histogram pattern that is useful to identify additional cell populations or subtypes in hematological analysis.
Figure 8B:
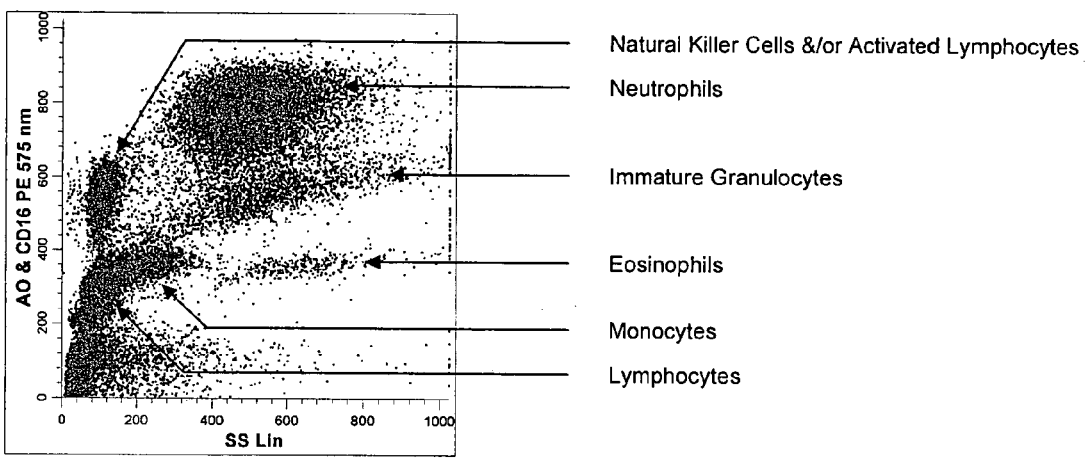
Figure 8C:
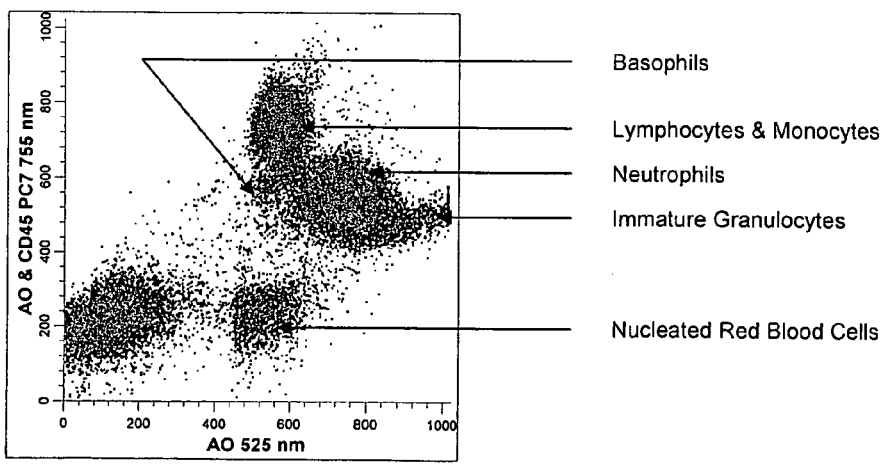

FIGS. 8A thru 8C are dual parameter histograms displaying the results of this experiment. FIG. 8A displays AO fluorescence at a wavelength of approximately 525 nm vs. SS. At least four cellular populations are identified and enumerated in this display: lymphocytes, monocytes, neutrophils and eosinophils. FIG. 8B displays AO & CD16-PE fluorescence at a wavelength of approximately 575 nm vs. SS. At least six cellular populations are identified and enumerated: lymphocytes, monocytes, eosinophils, neutrophils, immature granulocytes and a cluster containing natural killer cells and/or activated lymphocytes. FIG. 8C is a two parameter histogram generated from the experiment described in Example 8, displaying AO & CD45PC7 fluorescence at a wavelength of approximately 755 nm vs. AO fluorescence at a wavelength of approximately 525 nm. At least five cellular populations are identified and enumerated: a cluster containing lymphocytes and monocytes, basophils, neutrophils, immature granulocytes and nucleated RBCs.

Example 9

A single reaction mixture was prepared by reacting 100 µL of an abnormal human peripheral blood specimen with about 1 µg of anti-CD45-PE, the first antibody, and about 1 µg of anti-CD16-PC7, the additional antibody labeled with a second fluorochrome having a different peak emission spectrum than PE. The reaction mixture was then contacted with approximately 1.25 µg/mL of Acridine Orange, which has an emission spectrum that overlaps with the peak emission spectrum of PE to form a novel non-compensatable spectral pattern. This reaction mixture is mixed briefly and incubated at room temperature for approximately 10 minutes.

This reaction mixture is then reacted for about 8 seconds with the lytic system (about 600 µL of Immunoprep™ reagent A; see U.S. Pat. No. 5,030,554) that differentially lyses the non-nucleated red blood cells in the blood specimen while conserving the desired intrinsic and extrinsic properties of the nucleated cell populations including leukocytes and nucleated red blood cells. After about 8 seconds, the quenching reagent (Immunoprep™ reagent B; 265 µL) is introduced into the mixture for 10 seconds, to terminate the lytic reaction. No fixation was used.

Thereafter, the mixture is allowed to flow into a transducer module that is capable of making multiple correlated measurements (fluorescent and optical) on cells as they pass through a single aperture in the transducer module.

Figure 9A:
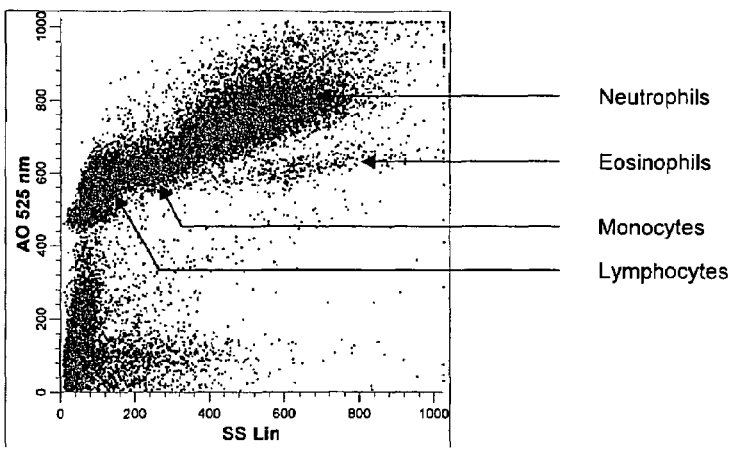
FIGS. 9A thru 9C are dual parameter histograms obtained by performing a method described herein in which an abnormal peripheral blood specimen was reacted with a first antibody labeled with a first fluorochrome (CD45-PE) having a first peak emission spectrum. The first antibody binds to an antigenic determinant that is differentially expressed on populations of leukocytes and non-leukocytes. An additional antibody labeled with an additional fluorochrome (CD16-PC7), binds to an antigenic determinant that is differentially expressed on populations of mature and immature granulocytes or myeloid cells. The additional fluorochrome has an additional peak emission spectrum distinguishable from the first peak emission spectrum. The fluorescent dye (Acridine Orange) which has a peak emission spectrum that overlaps with the peak emission spectrum of PE and a lytic system that differentially lyses any non-nucleated red blood cells present in the sample and conserves the leukocyte population in the sample are also used. As provided above, the overlap between AO and PE forms a new non-separable spectral emission. This new fluorescent footprint is a result of the overlapping spectra and the combined cellular staining patterns of the dyes and fluorochrome labeled antibodies chosen for the composition. The new fluorescent footprint results in histogram patterns that are useful for the identification of additional cell populations or subtypes in hematological disease.
Figure 9B:
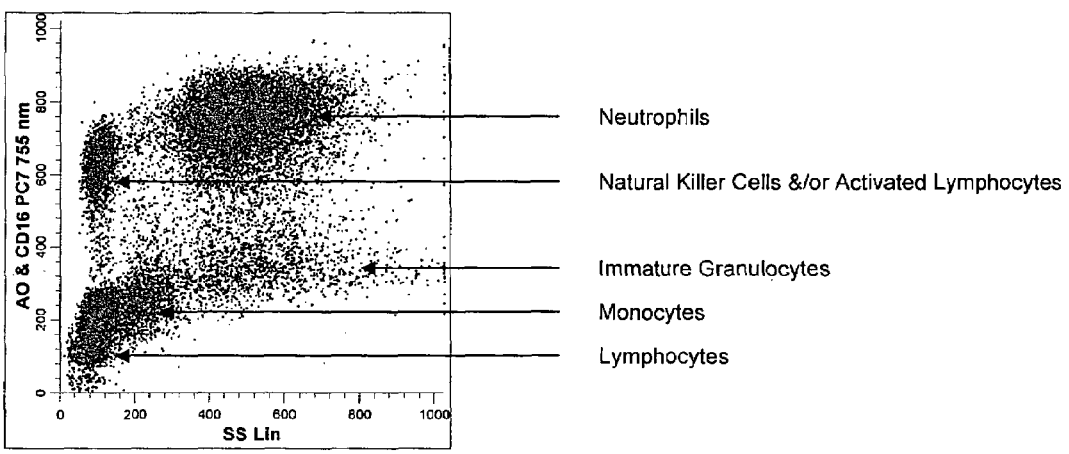
Figure 9C:
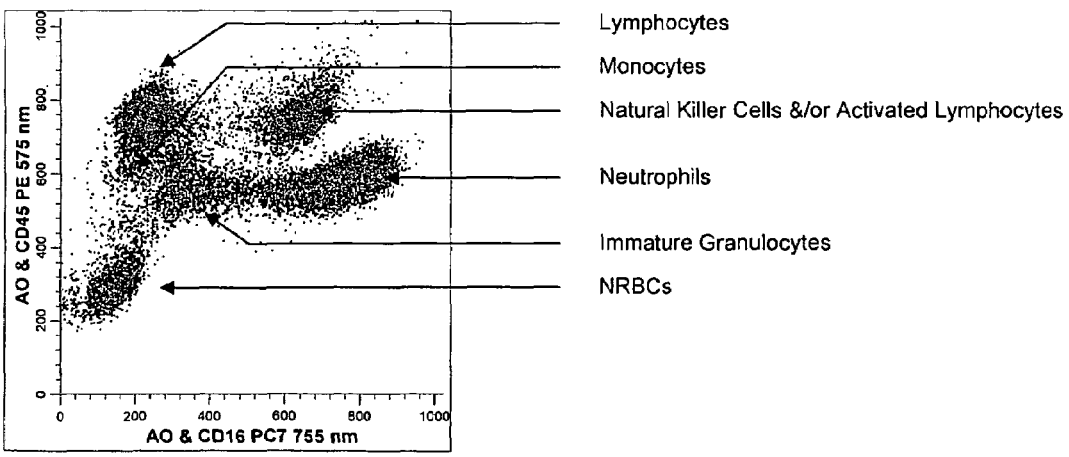

FIGS. 9A thru 9C are dual parameter histograms displaying the results of this analysis. FIG. 9A displays AO fluorescence at a wavelength of approximately 525 nm vs. SS. At least four cellular populations are identified and enumerated in this display: lymphocytes, monocytes, neutrophils and eosinophils. FIG. 9B displays AO & CD16-PC7 fluorescence at a wavelength of approximately 755 nm vs. SS following removal of the eosinophils by gating them out from FIG. 9A. At least five cellular populations are identified and enumerated: lymphocytes, monocytes, neutrophils, immature granulocytes and a cluster containing natural killer cells and/or activated lymphocytes. FIG. 9C displays AO & CD16-PC7 fluorescence at a wavelength of approximately 755 nm vs. AO & CD45-PE fluorescence at a wavelength of approximately 575 nm following removal of the eosinophils by gating them out from FIG. 9A. At least six cellular populations are identified and enumerated: lymphocytes, monocytes, neutrophils, immature granulocytes, nucleated red blood cells and a cluster containing natural killer cells and/or activated lymphocytes.

In alternative assays in which anti-CD19 is employed as one of the antibodies of the method (data not shown), the effect of the presence of the anti-CD19 to monoclonal is detected by the separation of the lymphocyte population into B and non-B cell populations. In atypical specimens this permits the observation of a distinction between B cell and non-B cell blasts, chronic and acute B cell disorders and the presence of atypical lymphocytes of B cell lineage.

This method may be used to detect blasts. Several optical and electrical parameters in conjunction with anti-CD45 fluorescence expression provide the necessary separation of blasts from normal cell types and debris, which is required to make this determination. Anti-CD19 antibody provides this method with the ability to categorize the blasts as lymphoid blasts of B cell lineage based on the expression of CD19. In exemplary abnormal blood specimens, the blasts can demonstrate CD19 expression that is higher than the non-B normal lymphocytes but equal to or less than that of the normal B cells in this specimen. Using this information, the blasts may be enumerated and categorized and then gated out of other views so that the normal 5-part differential may be recovered. Other scattergrams may be generated on similar abnormal samples to detect blasts distinctly from debris and other cell types in the abnormal peripheral blood specimen. The blasts may be further characterized as being of non-B cell lineage. This is determined by scattergrams showing that the blasts display CD19 expression that is equal to or less than non-B cells.

Results from other analyses (not shown, but described in U.S. Patent Application No. 60/573,167, incorporated herein by reference) are also summarized in the examples below.

Example 10

The method of one embodiment was conducted on four different biological specimens, i.e., (1) normal peripheral blood, (2) a B lymphoblastic leukemia specimen, (3) a B chronic lymphocytic leukemia (BCLL) specimen containing mostly small lymphocytes and (4) a BCLL with prolymphocytic transformation displaying a high percent of large lymphocytes. The method employed three antibodies, namely anti-CD45PECy5, anti-CD16PE and anti-CD19PE, according to the method including the lytic system described above in Examples 3 and 4. For each sample, five scattergrams were generated using the parameters as follows: DC vs. RLS, DC vs. Opacity (RF), fluorescence of anti-CD45PECy5 vs. SS, fluorescence of anti-CD45PECy5log vs. SS, and DC vs. fluorescence of CD16PE and CD19PE (data not shown).

The scattergrams of the normal sample illustrated the 5 normal populations of lymphocytes, basophils, eosinophils, neutrophils and monocytes, as well as B cell and non-B cell (lineage) populations.

The scattergrams of the B Cell lymphoblastic leukemia sample containing blasts of B cell lineage enumerated the normal 5 populations, as well as blasts, blasts of B-cell lineage, NK cells, and other B cells, and non-B cell populations.

The scattergrams of the B Cell chronic lymphocytic leukemia sample containing 1% atypical lymphocytes enumerated the normal 5 populations, as well as a population of numerous small B lymphocytes that do not exhibit a CD45 blast pattern and non-B cell populations. The method is able to correctly recategorize what the manual differential regarded as atypical lymphocytes as abnormal B cells. These leukemic cells may have a slightly lower CD45 expression than normal lymphocytes and most often are composed of small cells that also display impedance characteristics equal to or lower than small lymphocytes. When normal lymphocytes are present in significant numbers, or these types of CLL cells are present in relatively low numbers, this may result in a double lymphocyte peak in DC as well as in forward scatter. These cells, while slightly lower in CD45 expression, do not express the typical blast pattern (extremely weak or negative CD45 and increased scatter). Since these CLLs are almost always of B cell lineage (greater than 98 or 99%), they appear as CD19 positive cells.

The scattergrams of the B Cell chronic lymphocytic leukemia sample containing 52% atypical lymphocytes, by manual differential, demonstrate the same effect of recategorizing cells previously designated as atypical lymphocytes or blasts as abnormal large B cells. This less common variety of CLLs has a mixture of small and large lymphocytes. As in the variety that is predominantly small cells, these cells do not express the typical blast patterns that have been demonstrated and are almost always CD19 positive. Therefore these cells may be distinguished from blasts and other cell types found in peripheral blood by this method.

Therefore, the method has the ability to detect and identify blasts and this most prevalent variety of BCLL cells from each other as well as the other cell types found in peripheral blood. Non-BCLLs of this variety (small cells) will also be detected but appear as CD19 negative. These types of small cell CLLs may therefore also be described (flagged) electronically as atypical lymphocytes. This method therefore permits positive detection of the most clinically significant varieties of atypical lymphocytes as well as distinguishing between different forms of atypical lymphocytes (blast vs. CLL cells) vs. activated cells. Thus this method clarifies the diagnosis of these disorders.

Previous experiments compared the results of pathology consultations based upon combining morphological examination with special stains, chromosomal analysis and leukemia phenotyping by traditional flow cytometry with use of the method of an embodiment described herein. Such comparison demonstrated that the method used herein has an excellent ability to distinguish between blasts of B cell and non-B cell lineages.

Example 11

An Extended Differential on a flow cytometry based hematology system is obtained by forming a reaction mixture as follows. 100 μL of peripheral blood sample that contains 18 percent immature granulocytes (9% myelocytes and 9% metamyelocytes) is combined with AO, anti-CD45 PECy7 and anti-CD16 PECy7 in the same concentrations as described in the Examples 5-9 above.

This reaction mixture is mixed briefly and incubated at room temperature for approximately 10 minutes. At the end of the incubation period the reaction mixture is exposed to a lytic reagent (lyse and quench) to eliminate non nucleated RBC from the analysis and then analyzed on a flow cytometry system capable of measuring 5 channels of fluorescence in combination with side scatter (90 degrees) and forward angle scatter (2-18 degrees). The example utilizes a blue argon ion laser as an excitation source for the fluorescence detection.

The data (not shown) is displayed with side scatter on the horizontal axis and fluorescence on the vertical axis. In the 755 nm fluorescence channel immature granulocytes can be identified as a population of cells with less fluorescence and greater side scatter than mature granulocytes. In contrast the mature and immature granulocyte populations have overlapping fluorescence signatures in the 525 nm and 675 nm channels. There is improved separation of monocytes in the 675 nm channel compared to the spatial separation observed in the 525 nm channel.

This improved separation of monocytes in the 675 nm channel was used to remove this population from the histogram presented for the 755 nm channel. This technique removed the monocyte population overlap and aided in the identification and enumeration of mature and immature granulocyte populations in the 755 nm channel.

Thus, a method described herein is capable of identifying monocytes, mature granulocytes and immature granulocytes, as well as the other cell populations identified in the preceding examples.

Example 12

An Extended Differential on a flow cytometry based hematology system is obtained by forming a reaction mixture as follows. 100 μl of peripheral blood sample that contains predominantly blasts and a small number of lymphocytes is combined with AO, anti-CD45 PECy7 and anti-CD16 PECy7 in the same concentrations as described in Examples 5-9.

This reaction mixture is mixed briefly and incubated at room temperature for approximately 10 minutes. At the end of the incubation period the reaction mixture is exposed to a lytic reagent (lyse and quench) to eliminate non nucleated RBC from the analysis and then analyzed on a flow cytometry system capable of measuring 5 channels of fluorescence in combination with side scatter (90 degrees) and forward angle scatter (2-18 degrees). The example utilizes a blue argon ion laser as an excitation source for the fluorescence detection.

Data from three selected fluorescence channels (not shown) was displayed with side scatter on the horizontal axis and fluorescence on the vertical axis. It is evident from examination of the data in the 755 nm channel that blasts appear as a cell population with less fluorescence than lymphocytes but with a side scatter signature that is larger than most small lymphocytes. This pattern is due to the decreased expression of the CD45 antigen on blasts. It is also evident from examining the data provided by the 525 nm and 675 nm channels that the blasts patterns are overlapping the lymphocyte population and do not appear as a distinct population. In this example the blast specimen demonstrates a bimodal distribution in these channels which is due to the age or fragility of the specimen.

Example 13

An abnormal peripheral blood specimen containing immature granulocytes and blasts was stained with AO and CD45 PC7 and CD16PC7 (two different antibodies with the same fluorochrome overlapping with AO in the 755nm region) according to the methods described herein and using the same concentrations as those of Example 5-9 above. Both specimen examples were lysed using the Immunoprep™ reagent system and specimen preparation was the same as that described in the prior examples.

The results of this analysis (not shown) indicate that a method described herein is capable of identifying and enumerating multiple cellular abnormalities in a single analytical evaluation.

Example 14

A normal peripheral blood specimen was stained with AO and CD45 PC7 and CD16PC7 (two different antibodies with the same fluorochrome, i.e., overlapping peak emission spectra which do not overlap with the emission spectrum of AO) and using the same concentrations as those of Examples 5-9 above. An aliquot of the same specimen was stained with AO and CD45 PC7 & CD16 PE (i.e., one antibody labeled with PE, which has a peak emission spectrum that overlaps the emission spectrum of AO and forms a non-compensatable spectral pattern; and one antibody labeled with PC7, which has a peak emission spectrum that is distinguishable from the emission spectrum of AO). Both specimen examples were lysed using the Immunoprep™ reagent system and specimen preparation was the same as that previously described.

The results (not shown) indicate a difference in eosinophil/neutrophil separation depending upon the fluorochrome to which the CD16 antibody is conjugated. This demonstrates two distinct examples of the principal of additive fluorescence and offers different analytical opportunities for detection and enumeration of normal and atypical cell populations.

Example 15

A peripheral blood specimen containing immature granulocytes, nucleated red blood cells and blasts was reacted with a composition comprising a single anti-CD16 antibody labeled with a fluorochrome (CD16-PE). The antibody binds to an antigenic determinant that is differentially expressed on populations of mature and immature granulocytes or myeloid cells. The composition includes a fluorescent dye (Acridine Orange) which has an emission spectrum that overlaps with the antibody-PE peak emission spectrum to form a non-compensatable spectral pattern. The reaction mixture was then contacted with a lytic system that differentially lyses non-nucleated red blood cells present in the sample and conserves the nucleated cell populations including leukocytes and nucleated red blood cells. The sample was then passed through a single flow aperture in a flow hematology analyzer.

Figure 10:
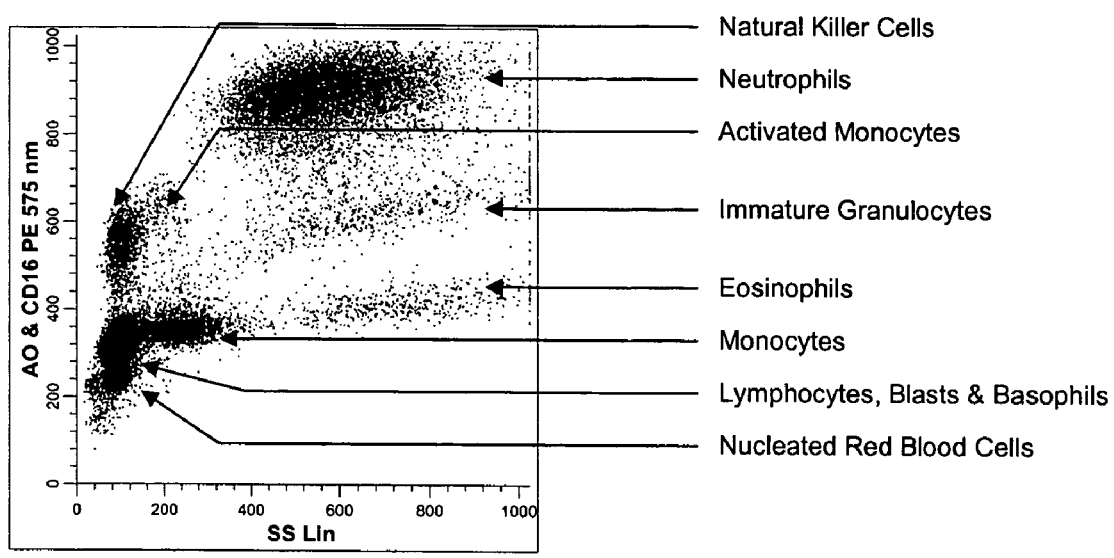
FIG. 10 is a dual parameter histogram displaying AO and CD16-PE fluorescence at a wavelength of approximately 575 run vs. SS generated from the experiment of Example 15 (using a single anti-CD16-PE antibody, a nucleic acid dye that overlaps the peak emission spectrum of PE, and a lysis reagent). Using the new "footprint" formed as described herein, at least eight cellular populations are identified and enumerated in this display: neutrophils, immature granulocytes, eosinophils, natural killer cells, activated monocytes, monocytes, nucleated red blood cells and a cluster containing lymphocytes, blasts and basophils.

The results are shown in the dual parameter histogram of FIG. 10, which displays AO and CD16-PE fluorescence at a wavelength of approximately 575 nm vs. SS. At least seven cellular populations are identified and enumerated in this display: neutrophils, immature granulocytes, eosinophils, a cluster containing natural killer cells and/or activated lymphocytes, activated monocytes, monocytes, nucleated red blood cells and a cluster containing lymphocytes, blasts and basophils.

Example 16

A peripheral blood specimen containing nucleated red blood cells and blasts was reacted with an anti-CD45 antibody labeled with a fluorochrome (CD45-PE). The antibody binds to an antigenic determinant that is differentially expressed on populations of leukocytes and non-leukocytes. A fluorescent dye Acridine Orange, which has an emission spectrum that overlaps with the peak emission spectrum of PE so as to form a non-compensatable spectral pattern, is included in the composition. The reaction mixture was then contacted with a lytic system that differentially lyses non-nucleated red blood cells present in the sample and conserves the nucleated cell populations including leukocytes and nucleated red blood cells. The sample was then passed through a single flow aperture in a flow hematology analyzer.

The results are depicted in FIGS. 11A and 11B, which are two parameter histograms displaying AO fluorescence at a wavelength of approximately 525 nm vs. SS, and AO and CD45-PE fluorescence at a wavelength of approximately 575 nm vs. SS, respectively. FIG. 11A identifies and enumerates at least four cellular populations: neutrophils, eosinophils, monocytes, nucleated red blood cells, and a cluster containing lymphocytes, blasts and basophils. FIG. 11B identifies and enumerates at least five cellular populations: lymphocytes, monocytes, basophils, blasts, nucleated red blood cells and a cluster of granulocytes containing neutrophils and eosinophils. Based upon the above data, by using the combination of CD45-PE and Acridine Orange, one can identify and enumerate at least seven discrete cellular populations.

The above examples illustrate the principle of additive fluorescence, including specifically the embodiment in which an overlap between a fluorescent dye emission spectrum and the peak emission spectrum of a fluorochrome, or an overlap between two fluorochromes, forms a non-compensatable spectral pattern. Other examples of additive fluorescence are also provided by the various combinations of labeled antibodies with and without the dye as discussed herein. A new fluorescent footprint is a result of the overlapping spectra and the combined cellular staining patterns of the dyes and fluorochrome labeled antibodies chosen for the composition. The new fluorescent footprint results in histogram patterns that are useful for the identification of additional cell populations or subtypes in hematological disease. Various methods described herein employ the new footprint to obtain specific information. The use of the compositions described herein can alter or enhance the patterns in other fluorescence channels to obtain new information.

In summary, novel analytical methods for determining comprehensive extended differentials are provided. These methods combine the analytical advantages provided by fluorescent dyes and monoclonal antibodies into a single unified approach that is superior to either method alone.

All published documents, patents and patent applications, as well as the disclosures of the priority documents recited above, are incorporated herein by reference. Numerous conventional modifications and variations of the methods and compositions described herein are included in the above-identified specification and are expected to be obvious to one of skill in the art. Such modifications and alterations to the compositions and processes of the various embodiments of the invention are believed to be encompassed in the scope of the claims appended hereto.

The invention claimed is:

1. A kit for differentially identifying cells in an instrument comprising:
    (a) a fluorescent dye capable of staining cells, which has a dye emission spectrum;
    (b) a first antibody that binds to an antigenic determinant that is differentially expressed on a first population of blood cells, the antibody labeled with a first fluorochrome having a first peak emission spectrum; and
    (c) an optional additional antibody that binds to a second antigenic determinant that is differentially expressed on a second population of blood cells, the additional antibody labeled with a second fluorochrome having a second peak emission spectrum, wherein the second peak emission spectrum is the same as the first peak emission spectrum or different from the first peak emission spectrum;
    at least two spectra selected from the group consisting of said dye emission spectrum of (a), the first peak emission spectrum of (b) and the second peak emission spectrum of (c) overlap to form a spectral pattern that cannot be separated by optical or color compensation methods.

2. The kit according to claim 1, wherein said dye emission spectrum of (a) overlaps said first peak emission spectrum of (b) to form a spectral pattern that cannot be separated by optical or color compensation methods, and said additional antibody (c) is absent or is labeled with said same fluorochrome.

3. The kit according to claim 1, wherein said first peak emission spectrum of (b) overlaps the second peak emission spectrum of (c) to form a spectral pattern that cannot be separated by optical or color compensation methods, and neither the first nor second peak emission spectrum overlaps the dye emission spectrum to form a spectral pattern that cannot be separated by optical or color compensation methods.

4. The kit according to claim 1, wherein said dye emission spectrum of (a) overlaps said second peak emission spectrum of (c) to form a spectral pattern that cannot be separated by optical or color compensation methods, and neither overlaps said first peak emission spectrum of (b).

5. The kit according to claim 1, wherein said dye emission spectrum (a) overlaps said first peak emission spectrum of (b) and said second peak emission spectrum of (c) to form a spectral pattern that cannot be separated by optical or color compensation methods.

6. The kit according to claim 1, wherein the first antibody (b) binds to an antigenic determinant that is differentially expressed on populations of leukocytes and non-leukocytes.

7. The kit according to claim 6, wherein the antibody that binds to an antigenic determinant that is differentially expressed on populations of leukocytes and non-leukocytes is an antibody selected from the group consisting of anti-CD45, anti-CD11a, anti-CD50, anti-CD18 anti-CD53, anti-CD62L and combinations thereof.

8. The kit according to claim 1, wherein the additional antibody (c) binds to a second antigenic determinant that is differentially expressed on populations of mature and immature granulocytes or myeloid cells.

9. The kit according to claim 8, wherein the antibody that binds to an antigenic determinant that is differentially expressed on populations of mature and immature granulocytes or myeloid cells is an antibody selected from the group consisting of anti-CD16 capable of binding both antigens $CD16\alpha$ and $CD16\beta$, anti-$CD16\alpha$, anti-$CD16\beta$, anti-CD11b, anti-CD15, anti-CD35 anti-CD24, anti-CD10, anti-CD49d, anti-CD64, anti-CD87 and combinations thereof.

10. The kit according to claim 1, further comprising more than one additional antibody (c).

11. The kit according to claim 1, wherein the fluorescent dye has one or more characteristics selected from the group consisting of a nucleic acid dye, a mitochondrial dye, an enzyme substrate dye, a metachromatic dye, a non-metachromatic dye, a cell-permeant dye, and a cell impermeant dye.

12. The kit according to claim 1, further comprising a lytic system comprising one or more reagents that differentially lyses non-nucleated red blood cells present in a blood sample and conserves the platelets and nucleated cell populations.

13. The kit according to claim 1, wherein the spectral pattern cannot be separated by optical compensation methods.

14. A composition for differentially identifying cells in an instrument comprising in admixture:
    (a) a fluorescent dye capable of staining cells, which has a dye emission spectrum;
    (b) a first antibody that binds to an antigenic determinant that is differentially expressed on a first populations of blood cells, the antibody labeled with a first fluorochrome having a first peak emission spectrum; and
    (c) an optional additional antibody that binds to a second antigenic determinant that is differentially expressed on a second populations of blood cells, the additional antibody labeled with a second fluorochrome having a second peak emission spectrum; wherein the second peak emission spectrum is the same as the first peak emission spectrum or different from the first peak emission spectrum;
    at least two spectra selected from the group consisting of said dye emission spectrum of (a), the first peak emission spectrum of (b) and the second peak emission spectrum of (c) overlap to form a spectral pattern that cannot be separated by optical or color compensation methods.

15. The composition according to claim 14, wherein the spectral pattern cannot be separated by optical compensation methods.

16. A method for the differentiation or enumeration of cell populations in a biological sample, said method comprising:
    (a) passing through a sensing region in a cell analyzer that is capable of making multiple correlated measurements on cells, a mixture comprising:
        i. the biological sample;
        ii. a fluorescent dye capable of staining cells, which has a dye emission spectrum;
        iii. a first antibody that binds to an antigenic determinant that is differentially expressed on a first population of blood cells, the antibody labeled with a first fluorochrome having a first peak emission spectrum; and
        iv. an optional additional antibody that binds to a second antigenic determinant that is differentially expressed on a second populations of blood cells, the additional antibody labeled with a second fluorochrome having a second peak emission spectrum, wherein the second peak emission spectrum is the same as the first peak emission spectrum or different from said first peak emission spectrum;
        wherein at least two spectra selected from the group consisting of said dye emission spectrum of (a), said first peak emission spectrum of (b) and said peak emission spectrum of (c) overlap at an emission wavelength to form a spectral pattern that cannot be separated by optical or color compensation methods;
    (b) detecting the fluorescence signals of said fluorochromes and dye and detecting at least one additional parameter which is an optical parameter, an electrical parameter, or combinations thereof, for the cells in the sample; and (c) analyzing the fluorescence of the dye and said fluorochromes at an emission wavelength within the non-separable overlapping spectral pattern that reveals additive fluorescence, with said at least one additional parameter to differentiate or enumerate populations of cells in said biological sample.

17. The method according to claim 16, wherein said passing step comprises passing said mixture through a single flow aperture in a flow hematology analyzer in a single step that measures the mixture for at least two of said parameters.

18. The method according to claim 16, further comprising retarding the effect of the lytic reagent by introducing a quenching reagent into the sample prior to the passing step.

19. The method according to claim 16, wherein the passing step measures multiple channels of fluorescence.

20. The method according to claim 16, further comprising contacting the reaction mixture with a sphering agent.

21. The method according to claim 16, wherein at least one antibody binds to an antigenic determinant that is differentially expressed on populations of leukocytes and non-leukocytes and at least one antibody binds to an antigenic determinant that is differentially expressed on populations of mature and immature granulocytes or myeloid cells.

22. The method according to claim 19, wherein at least one channel of fluorescence is excited with one of the group consisting of a blue laser, a green laser, or a red laser.

23. The method according to claim 16, wherein the spectral pattern cannot be separated by optical compensation methods.

24. A kit for differentially identifying cells in an instrument comprising:
  (a) a first antibody that binds to an antigenic determinant that is differentially expressed on leukocytes and non-leukocyte cells, said antibody labeled with a first fluorochrome having a first peak emission spectrum;
  (b) at least one additional antibody, which is
    (i) an additional antibody labeled with a fluorochrome having said first peak emission spectrum, wherein said additional antibody binds to an antigenic determinant that is differentially expressed on mature and immature granulocytes or myeloid cells;
    (ii) an additional antibody labeled with an additional fluorochrome, wherein said additional antibody binds to an antigenic determinant that is differentially expressed on mature and immature granulocytes or mycloid cells, and wherein said additional fluorochrome has a peak emission spectrum distinguishable from said first peak emission spectrum; or
    (iii) an additional antibody labeled with an additional fluorochrome, wherein said additional antibody binds to an antigenic determinant that is differentially expressed on mature and immature granulocytes or myeloid cells, and wherein said additional fluorochrome has a peak emission spectrum that overlaps the first peak emission spectrum; and
  (c) a nucleic acid dye which has a peak emission spectrum that overlaps the peak emission spectrum of at least one of said first fluorochrome and said additional fluorochrome.

* * * * *